United States Patent [19]
Morinaga et al.

[11] Patent Number: 4,789,636
[45] Date of Patent: Dec. 6, 1988

[54] DOUBLE-STRANDED DNA HAVING SEQUENCES COMPLEMENTARY TO A SINGLE-STRANDED DNA AND DERIVED FROM MUNGBEAN YELLOW MOSAIC VIRUS

[75] Inventors: Tsuto Morinaga, Sagamihara; Kin-ichiro Miura; Kunitada Shimotohno, both of Tokyo; Masato Ikegami, Funabashi; Yataro Ichikawa, Tokorozawa, all of Japan

[73] Assignee: Teijin Limited, Osaka, Japan

[21] Appl. No.: 647,829

[22] Filed: Sep. 5, 1984

[30] Foreign Application Priority Data

Sep. 5, 1983 [JP] Japan .................. 58-161945

[51] Int. Cl.$^4$ .................. C12N 15/00; C12P 21/00; C12P 19/34; C07H 21/04
[52] U.S. Cl. .................. 435/320; 435/68; 435/91; 435/172.1; 435/172.3; 536/27; 935/25
[58] Field of Search .................. 435/172.3, 317, 68, 435/70, 71, 91, 253, 172.1, 235, 317.1, 320; 536/27; 935/25

[56] References Cited
U.S. PATENT DOCUMENTS

4,237,224 12/1980 Cohen et al. .................. 435/68

OTHER PUBLICATIONS

Grierson et al. 1984, *Plant Molecular Biology*, Blackie, pp. 147-169.
Hull et al. 1983, "Genetic Engineering with Plant Viruses and their Potential as Vectors", *Adv. in Virus Res*, v 28, pp. 1-33.
Hamilton et al. 1984, "Complete Nucleotide Sequence of the Infectious Cloned DNA Components of Tomato Golden Mosaic Virus", EMBOJ V 3, pp. 2197-2205.
Howarth et al. 1985, "Nucleotide Sequence of Bean Golden Mosaic Virus and a Model for Gene Regulation in Geminiviruses", PNAS v 82, pp. 3572-76.
Mantell et al. (Ed s) 1983, *Plant Biotechnology*, Cambridge Univ. Press, pp. 299-312.
Panopoulous (Ed), 1981, *Genetic Engineering in the Plant Sciences*, Praeger, pp. 85-97.
Goodman 1977, "Single Stranded DNA Genome in a Whitefly-Transmitted Plant Virus", *Virology*, v 83, 171-79.
Goodman et al., 1980, "The Composition of Bean Golden Mosaic Virus and its Single-Stranded DNA Genome", *Virology*, v 106, pp. 168-72.
Reisman et al. 1979, "The Size and Topology of Single-Stranded DNA from Bean Golden Mosaic Virus", *Virology*, v 97, 388-95.
Haber et al. 1983, "Restriction Map and Southern Analysis of the Bean Golden Mosaic Virus Genome", Virology v 129, 469-73.
Stanley et al. 1983 "Nucleotide Sequence of Cassava Latent Virus DNA", *Nature* v 301, pp. 260-62.
Ikegami et al. 1983, "Isolation and Characterization of Virus-Specific Double-Stranded DNA from Tissue . . . ".
Ikegami et al. 1984, "Infectivity of Virus-Specific Double-Stranded DNA from Tissue Infected by Mungbean Yellow Mosaic Virus", (Abstract) Virus Res v 1(6) 507-12.
Taylor et al., "Efficient Transcription of RNA into DNA by Avian Sarcoma Virus Polymerase", Biochim. Biophys. ACTA 442: 324 (1976).

*Primary Examiner*—James Martinell
*Attorney, Agent, or Firm*—Wenderoth, Lind & Ponack

[57] ABSTRACT

Double-stranded DNA characterized by having sequences complementary to a single-stranded DNA which has a molecular size of about 2.67 Kb and is derived from mungbean yellow mosaic virus, and giving the restriction endonuclease cleavage map shown in FIG. 1 of the accompanying drawings; and double-stranded DNA characterized by having sequences complementary to a single-straned DNA which has a molecular size of about 2.70 Kb and is derived from mungbean yellow mosaic virus, and giving the restriction endonuclease cleavage map shown in FIG. 2 of the accompanying drawings; and hybrid DNAs having the double-stranded DNAs inserted thereinto.

14 Claims, 13 Drawing Sheets

——— : pBR 322

■■■ : dsDNA TMM-1 or dsDNA-a

——— : pBR 322

■■■ : dsDNA TMM-1 or dsDNA-a

— : YRp7

■ : dsDNA TMM-1 or dsDNA-a

— : YRp7

■ : dsDNA TMM-1 or dsDNA-a

— : Ylp 32

■ : dsDNA TMM-2 or dsDNA-b

— : Ylp 32

■ : dsDNA TMM-2 or dsDNA-b

DOUBLE-STRANDED DNA HAVING SEQUENCES COMPLEMENTARY TO A SINGLE-STRANDED DNA AND DERIVED FROM MUNGBEAN YELLOW MOSAIC VIRUS

BACKGROUND OF THE INVENTION

A. Field of the Invention

This invention relates to novel double-stranded derivatives of single-stranded DNAs derived from mungbean yellow mosaic virus (to be abbreviated as "MYMV") and to hybrid DNAs having the double-stranded derivatives inserted thereinto.

B. Description of the Prior Art

DNA genes from viruses have widely been developed and utilized as vectors in the gene recombination technology. Known viruses which give such vectors include, for example, papovaviruses such as simian virus (SV) 40 or polyoma virus, papilloma virus, and adenovirus. Since, however, these known vectors were discovered as animal vectors and do not replicate in plant cells, they cannot be utilized for gene recombination of plants.

The Ti-plasmid of an extranuclear gene possessed by *Agrobacterium tumefaciens* which forms tumors in dicotyledonous plants such as tomato and tobacco, and the DNA gene from cauliflower mosaic virus which causes diseases to cabbage or Chinese cabbage are the only vectors which have so far been known and have possible utilizability in plant gene recombination. No other suitable vector for plant gene recombination has yet been developed. It can be said furthermore that the above cauliflower mosaic virus is the only known plant virus having DNA genes which may possibly have utility as a vector for plant gene recombination.

Recently, Robert M Goodman et al. of University of Illinois reported that BGMV, a tropical plant virus, forms one virion from paired particles having a diameter of about 18 nm, and the genome of this virus was analyzed and found to be a circular single-stranded DNA having a size of about 2500 bases [Virology, 83, 171 (1977); Virology, 97, 388 (1979)].

Later, several kinds of plant viruses have been discovered in which paired particles having a diameter of about 18 nm form one virion and of which genes are circular and single-stranded. A group of these viruses are called "geminivirus group".

As stated above, only the cauliflower mosaic virus and geminiviruses are known as DNA-type viruses of plants, and the geminiviruses would be very promising as a goal of the development of vectors for use in plant gene recombination.

The Ti-plasmid and the cauliflower mosaic virus previously proposed in regard to vectors for use in plant gene recombination are limited to dicotyledonous plants as host plants to be infected. In contrast, the host range of the geminiviruses includes not only dicotyledonous plants but also monocotyledonous plants such as wheat and corn which are important cereals for man. Accordingly, it would seem very significant to use DNAs of these geminiviruses as vectors for plant gene recombination.

The cauliflower mosaic virus propagates in the cytoplasm of plant cells, whereas the geminiviruses do both in the cytoplasm and the nucleus. This suggests the high possibility that vectors of geminiviruses will be able to modify nuclear genes themselves of plants. If, therefore, the single-stranded DNA of the geminivirus can be used as a vector by converting it into a double-stranded DNA which is easy to handle technically in the gene recombination technology, it would be industrially valuable.

We noted that mungbean yellow mosaic virus (MYMV) is a kind of geminivirus, and made investigations on the gene of this virus. These investigations have led to the discovery that the gene of MYMV is composed of two kinds of single-stranded DNA. We have succeeded in isolating these single-stranded DNAs of MYMV. In order to use these DNAs as vectors in the gene recombination technology, we have done extensive works on the conversion of these two single-stranded DNAs into double-stranded DNAs which are technically easy to handle and on the insertion of these DNAs into other biological vectors and the propagation of the resulting hybrid DNAs in the host organisms.

SUMMARY OF THE INVENTION

Thus, according to this invention, there are provided (1) double-stranded DNA characterized by having sequences complementary to a single-stranded DNA which has a molecular size of about 2.67 kb and is derived from mungbean yellow mosaic virus, and giving the restriction endonuclease cleavage map shown in FIG. 1 of the accompanying drawings; and (2) double-stranded DNA characterized by having sequences complementary to a single-stranded DNA which has a molecular size of about 2.70 kb and is derived from mungbean yellow mosaic virus, and giving the restriction endonuclease cleavage map shown in FIG. 2 of the accompanying drawings.

Figure 1:
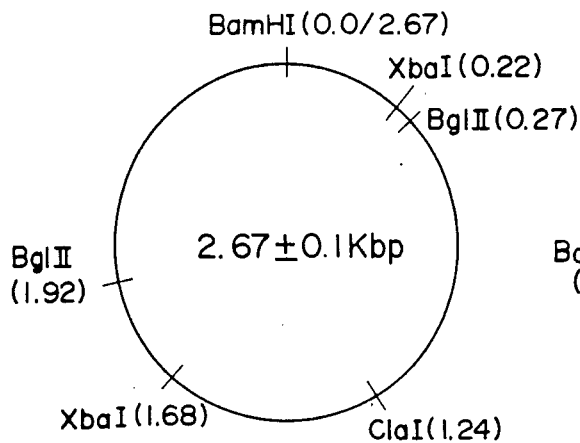
FIG. 1 is the restriction endonucloease cleavage map of the double-stranded DNA of the present invention characterized by having sequences complementary to a single-stranded DNA and having a molecular size of 2.67 kb.

Mungbean yellow mosaic virus (MYMV) is a kind of geminivirus discovered in Thailand. This virus causes a mosaic disease to mungbean or Top Crop (*Phaseolus vulgaris* L. "Top Crop"). It is deposited in Institute for Plant Virus Research of the Ministry of Agriculture and Fishery, Japan and is available from the depository. This virus can also be easily purified from an MYMV-infected plant in accordance with the same method as described in Phytopathology, 67, (No. 1), 37 (1977). From the purified virus, single-stranded DNAs can be separated and purified and converted to double-stranded DNAs by the following procedures.

(1). Separation of single-stranded DNAs from MYMV

The purified virus is shaken for 2 minutes with 30 mM Tris-HCl (pH 7.6); 1% SDS and 10 micrograms/ml of proteinase K. The proteins are extracted three times with phenol. The dissolved phenol is removed from the aqueous layer by ether extraction. Then, by ethanol precipitation, the single-stranded DNAs of the virus are separated and purified.

(2) Conversion of the single-stranded DNAs of MYMV into double-stranded DNAs

The single-stranded DNAs obtained as in (1) above are then converted to double-stranded DNAs in vitro by a modified version of a method known per se. As a first step, a primer as a starting site for double-stranding is bonded to the single-stranded DNAs. Generally, this primer can be used in an amount of 0.002 to 2,000 micrograms per microgram of the single-stranded DNAs.

One example of the primer which can be advantageously used in double-stranding the single-stranded DNAs of MYMV is oligonucleotides obtained by decomposing calf thymus DNA with DNase I in accordance with the method described in J. M. Taylor et al., Biochimica et Biophysica Acta, 442, 325 (1976). The oligonucleotides so obtained are in the double-stranded state, but can be easily single-stranded by heat-treating them under the conditions described below and can be bonded to a complementary site of the single-stranded DNAs of MYMV. Specifically, the single stranded DNAs of MYMV isolated as above are dispersed in water or a buffer such as an aqueous solution of Tris-HCl (pH 7.6-8.4) having a molarity of 30 to 300 mM, preferably 70 to 200 mM. The oligonucleotides are added to the dispersion. The mixture is then heated to a temperature of generally 50° to 80° C., preferably 60° to 70° C. and maintained at this temperature for about 1 to about 10 minutes, preferably about 3 to about 7 minutes. Then, as required, it is rapidly cooled to about 0° C. or below. As a result, the single-stranded DNAs of MYMV having the primer (oligonucleotides) bonded thereto are obtained.

When the oligonucleotides are used as the primer, their suitable amount is 50 to 400 micrograms, preferably 100 to 300 micrograms, per microgram of the single-stranded DNAs.

Water or the buffer is suitably used in an amount of generally 1 to 1000 microliters, preferably 10 to 500 microliters, per microgram of the single-stranded DNAs of MYMV.

Of course, the primer may also be a purified single-stranded DNA fragment containing at least 10 bases and having sequences quite complementary to the single-stranded DNA of MYMV. The amount of such a single-stranded DNA fragment used as a primer may generally be 0.002 to 1 microgram, preferably 0.004 to 0.02 microgram, per microgram of the single-stranded DNAs. When the purified complementary single-stranded DNA is used as the primer, the heat-treatment of a mixture of the single-stranded DNAs of MYMV and the primer is desirably carried out at a temperature of generally 40° to 70° C., preferably 55° to 65° C., for a period of about 5 to about 120 minutes, preferably about 20 to about 80 minutes.

To the single-stranded DNAs of MYMV having the primer bonded thereto in the above-described manner are added four deoxynucleotides, namely deoxyadenosine triphosphate (dATP), deoxycytidine triphosphate (dCTP), deoxyguanosine triphosphate (dGTP) and deoxythymidine triphosphate (dTTP), and they are reacted in the presence of an enzyme for double-stranding. These deoxynucleotides may be added to the single-stranded DNAs of MYMV before or after bonding the primer thereto either together with the primer or successively. The time of addition is not critical. The amount of each of these four deoxynucleotides may generally be 10 to 300 micro-M, preferably 50 to 150 micro-M, as the final concentration in the reaction solution.

Unless otherwise specified, "M" in the present specification denotes "mole/liter".

It is convenient in this reaction to replace part of dCTP by alpha-$^{32}$P-deoxycytidine triphosphate (alpha-$^{32}$P-dCTP) because it facilitates monitoring of the progress of double-stranding and the formation of double-stranded DNA in the subsequent reaction. To promote the double-stranding reaction, it is desirable in some cases to use Mg$^{++}$ (such as magnesium chloride or magnesium sulfate) in a concentration of 1 to 50 mM, preferably 5 to 20 mM.

Examples of the enzyme for double-stranding are a reverse transcriptase of avian myeloblastosis virus (AMV), T4-DNA polymerase, E. coli DNA polymerase I, and DNA polymerase I large fragment (Klenow Enzyme). Of these, the reverse transcriptase of AMV and DNA polymerase I large fragment are preferred.

The amount of the double-stranding enzyme depends mainly upon its type. For example, the effective amount of the reverse transcriptase of AMV (when Code 120248 made by Seikagaku Kogyo Co., Ltd. is used) is 1 to 20 units, preferably 5 to 10 units, per microgram of the single-stranded DNAs. If it is less than 1 unit, double-stranding is sometimes difficult to perform sufficiently.

The double-stranding reaction can be advantageously carried out by performing the reaction in the presence of the double-stranding enzyme first at a temperature of 10° to 30° C., preferably 15° to 25° C., and then at a temperature of 30° to 45° C., preferably 35° to 40° C., for 30 to 180 minutes, preferably 50 to 120 minutes.

Desirably, the pH of the reaction mixture during the reaction is maintained generally at 7.2 to 9.0, preferably at 7.6 to 8.4.

In the aforesaid double-stranding reaction, the ordinary enzyme stabilizers are effective. Examples are alpha-mercaptoethanol and dithiothreytol (DTT). The stabilizers may be used in a concentration of 0.1 to 5% by weight, preferably 0.5 to 2% by weight, in the reaction mixture.

To stop the reaction, a stopping agent such as water-saturated phenol or an aqueous solution of EDTA (pH 8.0) may be added to the reaction mixture. Water-saturated phenol is added in an amount 1/10 to 2 times the volume of the reaction mixture. The mixture is shaken and then only the aqueous layer is separated by centrifugation. The aqueous EDTA solution is used in an amount sufficient to capture $Mg^{++}$ present as a reaction promoter in the reaction mixture.

The double-stranded DNAs are separated by a method known per se, such as gel filtration, from the reaction mixture which has been subjected to the reaction stopping treatment described above. One specific example of this separating procedure will be described below.

The aqueous solution containing the double-stranded DNAs is fractionated using a gel-filtration agent such as Sephadex G-10 (a product of Pharmacia Fine Chemicals) or Biogel P30 (a product of Bio-Rad Laboratories), and the intensities of $^{32}P$ in the individual fractions are measured. Fractions containing high-molecular-weight DNAs having a high $^{32}P$ intensity which come out first in the individual fractions are collected, and precipitated in ethanol or isopropanol. As a result, double-stranded DNAs are obtained. The separated double-stranded DNAs sometimes contain a considerable amount of the primer DNAs, and this tendency is remarkable when the oligonucleotides from calf thymus DNA are used as the primer. Desirably, therefore, the double-stranded DNAs are again purified in this case in order to increase their purity. This purification can be carried out, for example, by the gel filtration procedure described above. One specific example is shown below. When 20 micrograms of single-stranded DNAs are used as a starting material, the separated double-stranded DNAs are dissolved in 100 to 500 microliters of water and subjected to gel filtration on a column having increased separability which is filled with Sephadex G-50 or Biogel P-30 equilibrated with 10 mM TrisHCl (pH 7.4) and 100 mM NaCl. As an eluent, 10 mM Tris-HCl (pH 7.4) and 100 mM NaCl are used. Fractions having a high $^{32}P$ count are collected from the void volume, and precipitated in ethanol or isopropanol to give highly pure double-stranded DNAs derived from MYMV.

(3) Characterization of the double-stranded DNAs

The geminivirus, MYMV, contains two kinds of single-stranded DNAs (to be referred to as "ssDNA-a" and "ssDNA-b"), and there are also two kinds of double-stranded DNAs obtained as shown above. The two double-stranded DNAs (to be referred to as "dsDNA-a" and "dsDNA-b" respectively) can be separated into the individual dsDNAs. They can be separated after cloning. Or it is possible to separate them before double-stranding (namely, while they are still single-stranded) and to double-strand them independently.

A mixture of single-stranded DNAs from MYMV can be separated into ssDNA-a and ssDNA-b by a method called "strand separation" (for example, the method described at pages 180 to 185 of Maniatis et al. "Molecular Cloning, A Laboratory Manual"), namely, gel electrophoresis, or a method which comprises adding a DNA fragment complementary to one of ssDNA-a and ssDNA-b to a cesium chloride solution of the DNA mixture, and separate it into the individual DNAs by equilibrium density gradient centrifugation utilizing the difference in density between the DNA which remains single-stranded and the partially double-stranded DNA.

The two DNAs derived from MYMV, however, are easier to separate after the mixture of single-stranded DNAs is double-stranded as described above and then the mixture of double-stranded DNAs is cloned, for example, in plasmid pBR322. This method of separation will be described in detail hereinafter.

Figure 2:
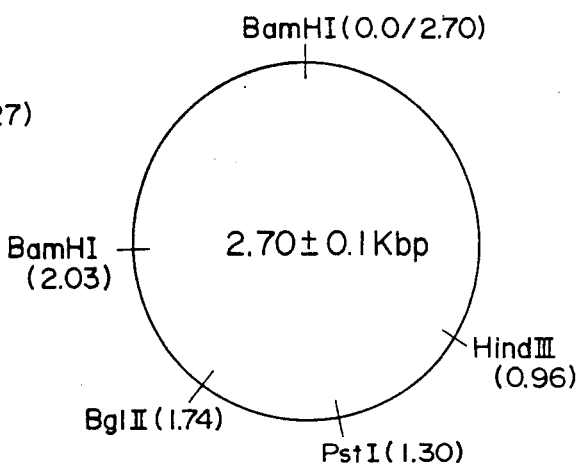
FIG. 2 is the restriction endonuclease cleavage map of the double-stranded DNA of the present invention characterized by having sequences complementary to a single-stranded DNA and having a molecualr size of 2.70 kb.

The two DNAs obtained by double-stranding DNAs from MYMV have a molecular size of 2.67±0.1 kilobase pairs (to be abbreviated as "Kbp") and 2.70±0.1 Kbp and give the restriction endonuclease cleavage maps shown in FIGS. 1 and 2 respectively of the accompanying drawings.

Furthermore, the above two DNAs show the cleavage patterns and restriction fragment sizes with regard to various restriction enzymes as shown in Table 1 below.

In Table 1, fragments which appeared high in density for their sizes in electrophoresis are classified as dsDNA-a, and others, as dsDNA-b.

TABLE 1

| Restriction enzyme | Fragment DNA size (Kbp) | |
|---|---|---|
| | dsDNA-a | dsDNA-b |
| Bam HI | 2.65 | 2.03, 0.69 |
| Bgl II | 1.65, 1.05 | 2.70 |
| Pst I | (3.3) | 2.68 |
| Xba I | 1.48, 1.19 | (3.3) |
| Cla I | 2.67 | (3.3) |
| Hind III | (3.3) | 2.69 |
| Xmn I | 2.65 | 1.92, 0.77 |
| Nar I | 2.65 | 2.70 |
| Hpa I | (3.3) | 2.70 |
| Nco I | 2.66 | 2.71 |
| Ava I | 2.67 | (3.3) |
| Bgl I | 2.65 | (3.3) |
| Mbo I | 0.95, 0.46, 0.32, 0.31, 0.19, 0.19, 0.18, 0.08 | 0.51, 0.46, 0.26, 0.23, 0.23, 0.22, 0.21, 0.20, 0.12, 0.12, 0.06, 0.06, 0.06, 0.04 |
| Bgl II/Pst I | 1.65, 1.05 | 2.28, 0.44 |
| Bam HI/Xba I | 1.47, 0.98, 0.22 | 1.98, 0.70 |
| Bam HI/Pst I | 2.65 | 1.27, 0.75, 0.68 |
| Bam HI/Bgl II | 1.65, 0.75, 0.27 | 1.72, 0.70, 0.29 |
| Bgl II/Xba I | 1.41, 0.96, 0.21, 0.05 | 2.70 |
| Hind III/Cla I | 2.65 | 2.65 |
| Hind III/Bgl II | 1.63, 1.02 | 1.95, 0.74 |
| Pst I/Xba I | 1.48, 1.22 | 2.65 |
| Cla I/Bgl II | 1.03, 0.97, 0.68 | 2.70 |
| Cla I/Xba I | 1.18, 1.04, 0.44 | (3.3) |
| Xmn I/Bam HI | 1.70, 0.97 | 1.61, 0.42, 0.35, 0.32 |
| Xmn I/Nar I | 1.65, 1.02 | 1.33, 0.77, 0.60 |
| Nar I/Bam HI | 2.62, ca. 0.05 | 1.02, 1.01, 0.67 |
| | Not digestible with Kpn I, Mlu I, Pvu II, Pvu I, Sal I, Xho I, Hind III, Pst I, Sac I, Sph I, Eco RV, Stu I, Nru I, Bcl I, Ban II, Apa I, Hpa I and Dpn I | Not digestible with Kpn I, Mlu I, Pvu II, Pvu I, Sal I, Xho I, Cla I, Xba I, Sac I, Bgl I, Sph I, Eco RV, Stu I, Nru I, Bcl I, Ava I, Apa I, and SmaI Dpn I, BstEII |

(*): With regard to the fragment size with Mbo I, not all of the fragments could be detected because the fragments were large in number and small in size. The table shows only the molecular sizes of fragments that could be detected.

The indication of (3.3) in the table shows that DNA remains open-ringed without undergoing cleavage and has an apparent molecular size of 3.3 Kbp with respect to the size marker of linear DNA.

It should be noted that the mesaured values for the sizes of the DNA fragments shown in the above table usually have a tolerance falling in range of ±0.05 Kbp.

Digestion with restriction enzymes such as Cla I, Sac I, Hpa I, Nar I, Nru I and Mbo I was carried out in a basic solution consisting of 10 mM Tris-HCl (pH 7.9), 7 mM $MgCl_2$, 7mM beta-mercaptoethanol, and 0.01% bovine serum albumin. Digestion with Hind III, Ava I, Kpn I, Pst I, Pvu II, Xmn I, Ban II, Sph I, Bgl I, Bcl I and Apa I was carried out in a mixture of the above-mentioned basic solution and 50mM of NaCl. Digestion with Sal I, Bam HI, Xba I, Xho I, Nco I, Eco RV, Stu I, Pvu I and Dpn I was carried out in a mixture of the basic solution and 150 mM of NaCl.

Hind III, Sal I, Bam HI, Kpn I, Pst I, Pvu II, Xho I, Hpa I and Stu I used in this invention were those manufactured by Takara Shuzo Co., Ltd. Ava I, Xba I and Dpn I were those manufactured by Bethesda Research Laboratories. Nco I and Ban II were those manufactured by Toyobo Co., Ltd. Nar I, Nru I and Xmn I were those manufactured by Nippon Gene Co. Sph I, Pvu I, Eco RV and Bcl I were manufactured by Boehringer Mannheim Co. Ltd.

In the present invention, all of the restriction enzymes for cleavage of DNA are used in an amount of at least 4 units per microgram of DNA, and the cleavage is carried out at 37° C. for at least 4 hours. When DNA is to be digested with two restriction enzymes, it is first digested with an enzyme for lower salt concentrations at 37° C. for at least 2 hours, and then with an enzyme for higher salt concentrations at 37° C. for at least 2 hours.

Fragment DNAs formed as a result of enzymatic digestion are analyzed by electrophoresis using 1.5% agarose gel containing 0.5 microgram/ml of ethidium bromide. At the time of this electrophoresis, rahmda-DNA digested with Eco RI/Hind III and plasmid pBR322 digested with Taq I were used as size markers of DNA.

The dsDNA-a and -b produced as above are substantially entirely double-stranded. Depending upon the manufacturing conditions, these DNAs may partly remain single-stranded. It should be understood that the double-stranded DNAs of this invention include those which partly remain single-stranded as above. Such DNAs can also be used in cloning or propagation as described hereinafter.

The double-stranded DNAs in accordance with this invention are used, for example, as vectors for plant gene recombination. For use as vectors, the DNAs are cleaved with certain enzymes. If at least those parts which are to be cleaved are double-stranded, those sites which are not double-stranded are repaired and almost completely double-stranded in the subsequent cloning or propagation. Accordingly, the double-stranded DNAs to be cloned or propagated may be double-stranded at least partly. Desirably, at least 80%, preferably at least 90%, of the base pairs of the single-stranded DNAs may be double-stranded.

The ratio between dsDNA-a and dsDNA-b differs depending upon the process of propagation of MYMV used as a starting material. Generally, the mole ratio of dsDNA-a to dsDNA-b is 2 or more. Accordingly, the assignment of the individual restriction fragments can be easily determined even by the action of a restriction enzyme on a mixture of dsDNA-a and dsDNA-b.

(4) Cloning of dsDNA-a and dsDNA-b

The dsDNA-a or -b produced as above is digested with a restriction enzyme capable of cleaving it preferably at a certain site, such as Hind III, Cla I, Bam HI, Bgl II or Pst I inserted into a host vector DNA cleaved with the same restriction enzyme. Examples of host vector DNAs that can be used in this case include plasmid vectors (such as pBR322, PBR328 and pBR325), cos-mid vectors (such as pKY2662) and pharge vectors (such as Sharon 10) for E. coli, plasmid vectors (such as pUB110, pUB112, pSA0501 and pTP4) for B. subtilis, and vectors for S. cerevisiae (such as YRp7, YIp32 and pYC2).

The term "host vector DNA", as used in the present specification and the attached claims, denotes a vector DNA that can have dsDNA-a or -b inserted thereinto to obtain a recombinant DNA which can be propagated in a host and from which dsDNA TMM-1 or TMM-2 can be reconstructed.

It is advantageous to use as the host vector DNA a vector DNA which has only one site (recognition site) capable of being cleaved with a restriction enzyme capable of cleaving dsDNA-a or -b only at one site.

There is used a host DNA which when recombined with dsDNA-a or -b, gives a hybrid DNA that self-propagates in a host microorganism such as *Escherichia coli*, *Saccharomyces cerevisiae* or *Bacillus subtilis*. Examples of such host DNAs include pBR322 [F. Bolivar et al., Gene 2, 95 (1977)], pBR325 [F. Bolivar, Gene 4, 121 (1978)], pBR328 [X. Sokeron et al., Gene, 9, (1980)], pMB9 [Rodriguez et al., Mol. Cell Biol., V. 471, Academic Press, New York (176)], pKY 2662 [L. S. Ozaki et al., Seika. 52, 770 (1980)] and pKC7 [Rao et al., Gene, 7, (1979)]; YRp7 and YIp32 [Struhl, K., et al., "Proc. Natl. Acad. Sci.", U.S.A., 76, 1035 (1979)], YEp13 [Broach et al: Gene, 8, 121 (1979)], and pYC1 and pYC2 Hohn, B. and Hennen, A.] of *Saccharomyces cerevisiae*; and pTA1060 and pTA1020 [Uozumi, T. et al., J. Bacteriol., 142, 315 (1980)], pC194, pC221, pC223 and pUB112 [Ehrlich, S. D., Proc. Natl. Acad. Sci., U.S.A., 74, 1680 (L977], pUB110 and pSA0501 [Gryczan, T. et al., J. Bacteriol., 134, 318 (1978)], pTP4 [Hoshino et al., Agric. Biol. Chem., 44, 2601 (1980)], and pE194 [Gryczan, T. et al., Proc. Natl. Acad. Sci., U.S.A., 25, 1428 (1978)] of *Bacillus subtilis*.

Preferably, there is only one site of cleavage with a restriction endonuclease both in dsDNA-a or dsDNA-b and the host vector DNA. Examples of such host vector DNAs are pBR322, pBR325, pBR328, YRp7, YIp32, pYC1, pTA1060, pC194, pC221, pC223, pUB110, pUB112 and pSA0501. Among these, pBR322, pB325, pBR328, YRp7, YIp32, pUB110 and pUB112 are especially preferred.

Now, the cloning of dsDNA-a and -b will be described in greater detail by taking up the E. coli plasmid vector pBR322 as a typical example.

First, dsDNA-a or -b is inserted into the plasmid vector to form a hybrid DNA. A hybrid DNA of dsDNA-a and pBR322 can be obtained by completely digesting dsDNA-a or a mixture of dsDNA-a and -b with one cut enzyme for dsDNA-a, for example, Bam HI, mixing the digestion product with the Bam HI-digestion product of a host vector DNA such as E. coli plasmid pBR322, and ligating them with a DNA ligase (such as T4-DNA ligase).

Likewise, a hybrid DNA of dsDNA-b and pBR322 can be obtained by completely digesting dsDNA-b or a mixture of dsDNA-a and -b with one cut enzyme for dsDNA-b, for example, Hind III, mixing the digestion product with the Hind III-digestion product of pBR322, and ligating them with a DNA ligase.

Desirably, the two DNAs to be ligated are mixed in nearly equimolar proportions because this can more efficiently lead to the desired hybrid DNA. Preferably, the host vector DNA, after cleavage with a restriction enzyme, is treated with an alkaline phosphatase to dephosphorylate the 5' terminal of DNA because this can almost completely prevent the self-ligation of the host vector DNA during the preparation of the hybrid DNA.

Using the resulting hybrid DNA, Escherichia coli HB101 is transformed in accordance with the method of M. Mandel and A. Higa [J. Mol. Biol., 53, 154 (1970)]. The transformants are cultivated on an agar (L-Agar) plate containing 50 micrograms/ml of an appropriate antibiotic such as ampicillin or tetracycline. The resulting colonies are subjected to colony hybridization in accordance with the method of Grunstein and Hogness (Proc. Natl. Acad. Sci., 72, 3961) using the $^{32}$P-labelled DNA of MYMV as a probe, and those colonies which have DNAs capable of being hybridized with the $^{32}$P-labelled DNA of MYMV are selected.

The plasmids which the selected colonies have are screened. The plasmid DNAs are separated from 1 ml of the colony overnight culture by performing "mini-preparation" by the so-called alkaline lysis method or the boiling lysis method.

The resulting plasmid DNAs are completely digested with one cut enzyme for dsDNA-a or dsDNA-b, for example, Bam HI or Hind III to select colonies having hybrid DNA containing DNA fragments with a size of about 2.67 Kbp or about 2.70 Kbp.

In this manner, it is possible to select Escherichia coli HB101 transformed with the hybrid DNA resulting from the ligation of dsDNA-a or dsDNA-b with plasmid pBR322 at the site of Bam HI or Hind III.

From the resulting transformants, the hybrid DNAs can be separated by a known method. The separated hybrid DNAs are almost completely double-stranded. They can be used to transform plant cells after introducing a foreign DNA into their specific site. They can be propagated within bacterial cells such as Escherichia coli cells.

The desired hybrid DNA can be prepared in large quantities by propagating the bacterial strain containing the hybrid DNA, as required performing an operation of amplifying only the hybrid DNA, subjecting the cells to lysis, and separating the hybrid DNA from an aqueous solution containing the hybrid DNA. Only a covalently closed circular (to be referred to as "ccc") hybrid DNA can be isolated by, for example, separating the hybrid DNA from the isolated E. coli transformants containing the hybrid DNA by using the methods of amplification and lysis of a hybrid DNA described at pages 88 to 94 of "Molecular Cloning—A Laboratory Manual" of Maniatis et al. (Cold Spring Harbor Laboratory 1982), and then subjecting it to equilibrium density centrifugation with cesium chloride.

The isolated hybrid DNA is digested with a restriction enzyme, Bam HI or Hind III to separate it into DNA fragments derived from dsDNA-a or -b and vector DNA fragments, and then isolating the DNA fragments derived from dsDNA-a or -b. When the digestion is performed with Bam HI, the digestion product is subjected to agarose gel electrophoresis, for example, and a slice of gel containing the DNA band of which DNA size is about 2.67 Kbp is cut off. Then, in accordance with the various methods decribed at pages 164 to 172 of the above-cited Manual of Maniatis et al., DNA fragments can be separated from the gel and purified. The desired cloned dsDNA-a can be obtained by ligating the DNA fragments with, for example, T4-DNA ligase by a method known per se. This cloned dsDNA-a forms a band having an apparent molecular size of about 3.3 Kbp by the agarose gel electrophoresis. By extracting DNA from the gel of this band portion and purifying it in the same way as above, the cloned dsDNA-a can further be purified.

On the other hand, a cloned dsDNA-b can be obtained by digesting the isolated hybrid DNA with Hind III, subjecting the digestion product to agarose gel electrophoresis in the same way as above, cutting off a slice of gel which contains about 2.70 Kbp sized DNA and treating the gel in the same way as above. This cloned DNA-b also forms a band having an apparent molecular size of about 3.3 Kbp by the agarose gel electrophoresis.

The cloned dsDNA-a and -b prepared by the above cloning operation are essentially the same as dsDNAs prepared in vitro from the ssDNAs of MYMV as stated in paragraph (2) above and the replicative form DNA of MYMV to be described hereinbelow in that they show the restriction endonuclease cleavage maps given in FIGS. 1 and 2 and the cleavage patterns given in Table 1. It has been found however that as shown in Table 2 they exhibit slightly different cleavage patterns with respect to restriction enzymes Dpn I and Mbo I. To distinguish them from each other, the cloned dsDNA-a and -b are referred to herein as dsDNA-a-1 and -b-1, and the dsDNA-a and -b prepared in vitro or being in the replicative form, as dsDNA-a-2 and -b-2. It should be understood that the dsDNA-a and dsDNA-b of this invention include dsDNA-a-1 and-2 and dsDNA-b-1 and -2.

TABLE 2

| | Fragment DNA size (Kbp) | |
|---|---|---|
| | Dpn I | Mbo I |
| dsDNA-a-1 | 0.95, 0.46, 0.32, 0.31, 0.19, 0.19, 0.18, 0.08 | Not digestibe |
| dsDNA-a-2 | Not digestible | 0.95, 0.46, 0.32, 0.31, 0.19, 0.19, 0.18, 0.08 |
| dsDNA-b-1 | 0.51, 0.46, 0.26, 0.23, 0.23, 0.22, 0.21, 0.20, 0.12, 0.12, 0.06, 0.06, 0.06, 0.04 | Not digestible |
| dsDNA-b-2 | Not digestible | 0.51, 0.46, 0.26, 0.23, 0.23, 0.22, 0.21, 0.20, 0.12, 0.12, 0.06, 0.06, 0.06, 0.04 |

The dsDNA-a and -b provided by this invention can be used either singly or in combination as a vector for plant gene recombination. Furthermore, a circular DNA having a foreign DNA at a specified site of dsDNA-a or -b can be formed by cleaving a specified restriction site of dsDNA-a or -b with restriction enzyme to form a linear DNA, mixing this DNA with a foreign DNA cut out by using the same restriction enzyme in nearly equimolar proportions, and ligating them with a DNA ligase (such as T4-DNA ligase) by a known method.

When, for example, the foreign DNA codes a gene which gives resistance to an antibiotic such as kanamycin or neomycin, plant cells can be transformed into kanamycin- or neomycin-resistant cells by using a DNA obtained by inserting the foreign DNA into dsDNA-a or -b. The transformation may be effected, for example, by the action of the DNA having the foreign DNA inserted thereinto upon the protoplasts of plant cells at a high pH in the presence of Ca$^{++}$ or in the presence of Ca$^{++}$; or by mechanically introducing the aforesaid DNA into the plant cells (micro-injection).

The dsDNA-a and -b provided by the present invention can be digested with a restriction enzyme preferably capable of cleaving one site of these DNAs, such as Hind III, Cla I, Bam HI, Bgl II, Bgl I or Pst I, and inserted into a host vector DNA (as exemplified below) cleaved with the same resriction enzyme. The host vector DNA used at this time may be those previously known, for example pBR322, pBR325, pBR328, pMB9, pKY2662, and pKC7 of *Escherichia coli;* YEp13, YRp7, YIp32, pYC1 and pYC2 of *Saccharomyces cerevisiae;* and pTA1060, pTA1020, pC194, pC221, pC223, pUB110, pUB112, pSA0501,and pE194 of *Bacillus subtilis.*

Preferred host vector DNAs are those which have only one cleavage site with an endonuclease as does the dsDNA-a or -b of the invention with the same endonuclease. Examples are pBR322, pBR325, pBR328, YRp7, pYC1, YIp32, pC194, pC221, pC223, pUB110 and pSA0501. Of these, pBR322, pBR325, pBR328, YRp7, YIp32, pUB110 and pUB112 are especially preferred.

A hybrid DNA can be prepared from the host vector DNA and dsDNA-a or -b by the same method as described before in cloning dsDNA-a or -b into pBR322.

The hybrid DNA so obtained may be utilized as a vector for various plants. Other foreign DNAs may further be inserted into the hybrid DNAs to utilize the latter more advantageously as vectors. Or they can be used for transforming plant cells by inserting other DNAs (sch as kanamycin- or neomycin-resistant genes, herbicide-resistant genes, etc.) for imparting useful properties as plants.

Now, the preparation of a hybrid DNA from the vector YRp7 or YIp32 of S. cerevisiae and the dsDNA-a and dsDNA-b will be described.

A mixture of dsDNA-a-2 and dsDNA-b-2 is digested with a restriction enzyme, Bam HI (the digestion product is referred to as "dsDNA(a+b)/Bam HI"). On the other hand, YRp7 is digested with Bam HI, and then treated with an alkaline phosphatase to dephosphorylate its 5' terminal (the product is referred to as "YRp7-/Bam HI").

The resulting dsDNA(a+b)/Bam HI and YRp7-/Bam HI are ligated with T4-DNA ligase. E. coli HB101 is transformed with the resulting hybrid DNA, and transformants resistant to ampicillin are selected. From the ampicillin-resistant transformants, those which are both ampicillin-resistant and tetracycline-sensitive are selected. The plasmid DNAs of the selected transformants are separated by the mini-preparation technique described above and completely digested with Bam HI. The resulting DNA fragments having a size of about 2.67 Kbp are self-ligated with T4-DNA ligase to obtain circular dsDNA-a-1.

Furthermore, a mixture of dsDNA-a-2 and -b-2 is digested with a restriction enzyme, Hind III (the digestion product is referred to as "dsDNA(a+b)/Hind III"). Separately, YIp32 is digested with Hind III, and its 5' terminal is treated with an alkaline phosphatase (the product is referred to as "YRp7/Hind III").

The resulting dsDNA (a+b)/Hind III and YIp32-/Hind III are ligated with T4-DNA ligase. E. coli HB101 is transformed with the resulting hybrid DNA, and those transformants which are resistant to ampicillin are selected. Then, colonies having DNAs capable of being hybridized with the $^{32}$P-labelled DNA of MYMV are selected by the aforesaid colony hybridization method using the $^{32}$P-labelled DNA of MYMV as a probe.

The hybrid DNA was separated from these selected colonies, and completely digested with Hind III. The resulting DNA fragments having a size of about 2.70 Kbp are self-ligated with T4-DNA ligase to obtain circular dsDNA-b-1.

The replicative form DNA of MYMV will now be described.

The replicative DNA of MYMV can be isolated from leaves infected with growing MYMV, for example the infected leaves of Top Crop (such as Top Crop of Takii Seed and Seedling Co., Ltd.) by using the method of D. O. Hamilton et al. [see Nucl. Acids Res. 10, 4902 (1982)] or the whole DNA extraction method described at pages 86 to 88 of Atsushi Hirai et al., "Introduction to Plant Cell Breeding" (a Japanese-language publication) published by Gakkai Shuppan Center. The whole DNA extracted by such a method is subjected to 0.8% agarose gel electrophoresis (at this time, the digestion product of lambda-DNA with Eco RI/Hind III is used together as a size marker of DNA). From this gel, DNA is transferred to a nitrocellulose filter by the Southern method [see E. M. Southern, J. Mol. Biol., 98, 503–517 (1975)]. Then, by the same procedure as described at pages 387 to 389 of "Molecular Cloning—A Laboratory Manual" of Maniatis et al. mentioned above using the $^{32}$P-labelled DNA of heat-denatured MYMV as a probe, DNA-DNA hybridization is carried out, followed by autoradiography by the same technique as the method described at pages 470 to 471 of the same book. The DNAs which are hybridized with the $^{32}$P-labelled DNA of MYMV appear as black bands on an X-ray film by autoradiography. These bands are therefore shown to be DNAs derived from MYMV. There are about 9 such bands observed, and they have an apparent size of >20 Kbp, 10 Kbp, 6.8 Kbp, 5.4 Kbp, 4.0 Kbp, 3.2 Kbp, 2.7 Kbp, 1.6 Kbp and 0.89 Kbp.

These DNAs are taken out from the agarose gel, and isolated from the gel by the same procedure as described hereinabove. When they are digested with any of Bam HI, Bgl II and Bgl II/Pst I, the same DNA fragments shown in Table 1 except a DNA corresponding to 0.89 Kbp can be obtained. Thus, the DNAs which give eight types of bands excepting the DNA corresponding to 0.89 Kbp are replicative DNAs of MYMV based on the DNAs shown in Table 1.

It is presumed that these replicative DNAs are in various forms, such as a covalently closed circle (c.c.c.), an open circle (o.c.), or a linear monomer, dimer or trimer. Of these bands, the band of 0.89 Kbp agrees with the single-stranded DNA of MYMV, but the others all correspond to double-stranded DNAs which are the replicative DNAs of MYMV.

Among the DNAs which give these bands, DNA corresponding to 1.6 Kbp, DNA corresponding to 3.2 Kbp, and DNA corresponding to 10.0 Kbp are present in relatively large amounts and can be easily utilized.

When the DNA corresponding to 1.6 Kbp, 3.2 Kbp or 10.0 Kbp is digested with Bam HI and cloned into the Bam HI cleavege site of E. coli plasmid pBR322, a hybrid DNA containing dsDNA-a-1 can be obtained. Likewise, a hybrid DNA containing dsDNA-b-1 can be obtained by digesting DNA corresponding to 1.6 Kbp, 3.2 Kbp, or 10.0 Kbp with Hind III and cloning it into the Hind III cleavage site of pBR322.

In the same way, a hybrid DNA containing dsDNA-a-1 can be obtained by digesting DNA corresponding to 1.6 Kbp, 3.2 Kbp or 10.0 Kbp with Bam HI, cloning it into the Bam HI cleavage site of a S. cerevisiae vector such as YRp7, propagating the clone in E. coli (such as E. coli HB101 strain), and treating the culture by a specified procedure. Furthermore, a hybrid DNA containing dsDNA-b-1 can be obtained by digesting DNA corresponding to 1.6 Kbp, 3.2 Kbp or 10.0 Kbp with Hind III, cloning it into the Hind III cleavage site of YIp32, propagating the clone in E. coli (such as E. coli HB101 strain), and treating the culture by a specified procedure.

The resulting hybrid DNAs can be used as vectors for various plants, or can be used as advantageous vectors by further inserting other foreign DNAs into them.

The dsDNA-a-1 and/or dsDNA-b-1 can be isolated from the resulting hybrid DNAs. The dsDNA-a-1 and/or dsDNA-b-1 has the same infectivity as MYMV.

The following experiments illustrate the present invention more specifically. It should be understood however that the invention is in no way limited to these specific experiments.

EXAMPLE

Ia. Separation and purification of virus

Top Crop (*Phaseolus vulgaris* L. "Top Crop") (53 g) infected with MYMV were ground in 250 ml of 0.1M sodium phosphate-10 mM EDTA buffer (pH 7.8) (containing 1.3 g of cysteine), and filtered through a double-layered gauze. The filtrate was centrifuged at 10000G for 40 minutes at 4° C. to obtain 205 ml of a supernatant. Sodium chloride (2.4 g) and then 8.2 g of polyethylene glycol (having a weight average molecular weight of 7800 to 9000) were added to the supernatant. The mixture was stirred at 4° C. for 1 hour, and then centrifuged at 10000G and 4° C. for 25 minutes. The supernatant was removed, and 10 ml of 0.1M sodium phosphate buffer (pH 7.8) was added to the precipitated polyethylene glycol pellet portion. The mixture was homogenized and centrifuged at 10000G and 4° C. for 30 minutes. The supernatant was centrifuged at 30,000 rpm in a Beckman SW 40.1 rotor to obtain a crude virus as a precipitate. The crude virus was homogenized in 0.5 ml of 0.1M sodium phosphate buffer (pH 7.8), and the mixture was subjected to 10-40% linear sucrose density gradient centrifugation at 32,000 rpm and 4° C. for 3 hours using the same SW 40.1 rotor. After the centrifugation, 0.6 ml fractions were separated from the bottom of the centrifugal tube. The absorbances $A_{260}$ of the fractions were measured. A peak assigned to the virus was observed in fractions Nos. 9 to 16. These fractions were combined, and 0.1M sodium phosphate buffer (pH 7.8) was added in an amount twice their amount. The mixture was homogenized and centrifuged by an SW 40.1 rotor at 35,000 rpm and 40° C. for 3 hours to obtain pellets of the virus again. These pellets were homogenized in 0.5 ml of 0.1M sodium phosphate buffer (pH=7.8), and again subjected to 10-40% linear sucrose density gradient using the SW40.1 rotor at 29,000 rpm and 4° C. for 3 hours. From the bottom of the centrifugal tube, 0.6 ml fractions were separated. Only a peak assigned to the virus was observed in fractions Nos. 13 to 18. These fractions were collected, and 0.1M sodium phosphate buffer (pH 7.8) was added in an amount twice their amount. The mixture was homogenized, and the virus was precipitated by means of the SW 40.1 rotor at 36,000 rpm and 4° C. for 3.5 hours to obtain purified MYMV.

Ib. Separation of a single-stranded DNA genome from virus and its purification To the purified MYMV obtained as above were added 750 microliters of sterilized water, 15 microliters of 1M Tris-HCl (pH 7.6), 75 microliters of 10% sodium dodecylsulfate (SDS) and 7.5 microliters of proteinase K (1 microgram/microliter solution). The mixture was shaken at room temperature for 2 minutes. Then, 700 microliters of phenol saturated with 10 mM Tris-HCl (pH 7.6)/1 mM EDTA aqueous solution was added, and the mixture was shaken for 3 minutes. The mixture was centrifuged for 5 minutes in an Eppendorf small-sized centrifuge, and the aqueous layer was collected. The aqueous layer was subjected to the same phenol extracting operation twice to obtain 950 microliters of the aqueous layer. Then, 700 microliters of chloroform was added to the aqueous layer, and the mixture was shaken for 2 minutes. The aqueous layer was taken out, and 700 microliters of ether was added to the aqueus layer to extract phenol. The extraction was repeated three times. To 1000 microliters of the aqueous layer were added 100 microliters of 3M sodium acetate buffer (pH 4.8) and 2.5 ml of ethanol, and the mixture was maintained for one day at $-20°$ C. The mixture was then centrifuged at 35,000 rpm for 20 minutes by a Beckman ultracentrifugal SW 50.1 rotor to precipitate the DNA. The DNA was dissolved in 400 microliters of 10 mM Tris-HCl/0.1 mM EDTA aqueous solution to form an aqeuous solution of a single-stranded DNA of MYMV in a concentration of 0.1 microgram/microliter.

Ic. Double stranding in vitro of the single-stranded DNA of MYMV

Ten microliters of the single-stranded DNA (0.1 microgram/microliter) of MYMV was mixed with 84 microliters of sterilized water, 30 microliters of 1M Tris-HCl (pH 8.0) and 12 microliters of DNA oligonucleotides (16.6 microgram/microliter) from calf thymus. (The DNA oligonucleotides from calf thymus will be explained hereinafer.) The mixture was maintained at 70° C. for 3 minutes, and then rapidly cooled to 0° C. While the mixture was maintained at 0° C., 30 microliters of 80 mM $MgCl_2$, 30 microliters of a 10% aqueous solution of beta-mercaptoethanol, 30 microliters of 0.8 mM deoxyadenosine triphosphate, 30 microliters of 0.8 mM deoxyguanosine triphosphate and 30 microliters of 0.8 mM deoxythymidine triphosphate, 10 microliters of 0.8 mM deoxycytidine triphosphate, 3 microliters of deoxycytidine 5'-[alpha-$^{32}$P] triphosphate (about 3000 Ci/mmole, 10 m Ci/ml, Code No. pB10205; a product of PabKmersham Japan Company) and 2 microliters of AMV reverse transcriptase (5 units/microliter; Code 120248 of Seikagaku Kogyo Co., Ldd.) were added. They were reacted at 20° C. for 10 minutes and then ant 37° C. for 1.5 hours. Then, 50 microliters of phenol was added and the mixture was shaken and centrifuged for 5 minutes in an Eppendorf centrifuge. The aqueous layer was gel-filtered. The gel filtration was carried out by using a column having a diameter of 6 mm filled with 5 ml of Sephadex G-75 (a product of Pharmacia Fine Chemicals) equilibrated with 10 mM Tris-HCl (pH 7.4)-0.1M NaCl aqueous solution. The aqueous layer was passed through the column and four-drop fractions were collected. The $^{32}$P intensity of each of the fractions was measured. The first peak appeared in fractions Nos. 6 to 12, and in fraction No. 14 and subsequent fractions, a peak assigned to the unreacted alpha-$^{32}$P-deoxycytidine triphosphate was observed. Fractions Nos. 6 to 12 were collected (about 700 microliters in total), and 60 microliters of 3M NaCl and 2.2 ml of ethanol were added. The mixture was maintained at −20° C. for 2 hours, and centrifuged at 30,000 rpm for 25 minutes (Beckman Ultracentrifuge SW50.1 rotor at 4° C.). The supernatant was removed, and 3 ml of a 70% aqueous solution of ethanol cooled to −20° C. was freshly added. The mixture was centrifuged at 20,000 rpm for 2 minutes, and the supernatant was removed. The precipitated DNA was dried under a reduced pressure of 20 mmHg for 1.5 minutes. The resulting DNA was dissolved in 100 microliters of 1 mM Tris-HCl (pH 7.4)/0.1 mM EDTA aqueous solution, and a DNA double-stranded in vitro was obtained (its $^{32}$P intensity was $32 \times 10^4$ cpm).

Preparation of DNA oligonucleotides of calf thymus

DNA (66 mg) of calf thymus was dissolved in 6.6 ml of a mixture of 0.1 M NaCl, 10 mM MgCl$_2$ and 10 mM Tris-HCl (pH 7.4), and 460 micrograms of DNase I (a product of Millipore Corporation; 2182 units/g) was added and incubated at 37° C. for 3 hours. The reaction was stopped by adding 0.66 ml of 0.2M EDTA. The reaction mixture was subjected to protein extraction with 7 ml of water-saturated phenol three times, and then the aqueous layer was extracted with three 7 ml portions of ether to remove phenol. Ethanol (20 ml) was added to the resulting aqueous layer. The mixture was left to stand at −20° C. for 2 hours, and centrifuged at 4000G for 4 minutes to obtain DNA pellets. The DNA pellets were dissolved in 0.5 ml of 0.1M NaCl and 10 mM Tris-HCl (pH 7.4), and subjected to gel filtration on a column (length 42 cm, diameter 0.5 cm) of Sephadex G-75 (a product of Pharmacia Fine Chemicals) equilibrated with 0.1 M NaCl and 10 mM Tris-HCl (pH 7.4). About 1.2 ml fractions were collected. A large peak was observed in fractions Nos. 10 to 32. Fractions Nos. 16 to 26 were collected (total amount 12.5 ml), and 31 ml of ethanol was added. The mixture was left to stand at −20° C. for 30 minutes, and then centrifuged at 4000G for 8 minutes. The resulting DNA pellets were dissolved in 1 ml of distilled water (DNA concentration 16.6 mg/ml). This solution was used as a primer DNA.

Ref. Ic-1

An experiment on double stranding was carried out under the same conditions as in experiment Ic above except that 12 microliters of the DNA oligonucleotides (16.6 microgram/microliter) of calf thymus was changed to 2 microliters. In experiment Ic in which the $^{32}$P count of the polymeric DNA portion was $2 \times 10^4$ cpm. It was found however that in this comparative experiment double stranding took place to an extent of less than one-tenth of that in the experiment Ic.

Ref. Ic-2

Double stranding was carried out in the same way as in experiment Ic above except that 40 microliters of a primer mixture (DNA concentration 5 microgram/microliter) from calf thymus DNA prepared by the method of J. M. Taylor et al. [Biochimica et Biophysica Acta, 442, 325 (1976)] was used instead of 12 microliters of the oligonucleotides (16.6 microgram/microlieter) in experiment Ic, and sterilized water was used in an amount of 55 microliters. The polymeric DNA portion had a $^{32}$P intensity of $13 \times 10^4$ cpm.

The double-stranded DNA obtained above was digested with each of restriction enzymes Bam HI, Hind III, Xba I and Bgl II and then subjected to autoradiography under the same conditions as in experiment Id described hereinbelow. The Hind III-digested DNA did not at all move from the well position of the agarose gel. Some DNAs digested with the other restriction enzymes stayed at the well position. The DNA which migrated considerably smeared the gel, and the band was not as clear as in experiment Id.

Id. Digestion of the double-stranded DNA with restriction enzymes, analysis of the digestion patterns and preparation of a restriction enzyme cleavage map To 3 microliters intensity 7300 cpm) of the $^{32}$P-labelled double-stranded DNA intensity $32 \times 10^4$ cpm/100 microliters) obtained in Ic were added 4 microliters of a restriction enzyme reaction buffer [for Cla I, Sac I and Mbo I, a standard solution composed of 100 mM Tris-HCl (pH 7.9), 70 mM MgCl$_2$, 70 mM beta-mercaptoethanol and 0.1% bovine serum albumin was used as the buffer; for Ava I, Hind III, Kpn I, Pst I, Pvu II, Xmn I, Ban II, Bgl II, Sph I, Bgl I and Apa I, a solution obtained by adding NaCl to 500 mM to the standard solution was used as the buffer; and for Sal I, Bam HI, Xba I, Xho I, Nco I, Eco RV, Stu I, Pvu I and Dpn I, a solution obtained by adding NaCl to 1500 mM to the standard solution was used as the buffer], 32 microliters of distilled water and 4 units of each of the restriction enzymes shown in Table 1, namely Ava I (2 units/microliter; units/microliter is abbreviated herein as U), Bam HI (6 U), Bgl II (6 U), Pst I (5 U), Xba I (6 U), Hind III (5 U), Kpn I (6 U), Pvu II (6 U), Sal I (6 U), Xho I (7.5 U), Cla I (5 U), Sac I (15 U), Mbo I (10 U), Xmn I (6 U), Ban II (2 U), Sph I (1.8 U), Bgl I (7.5 U), Apa I (20 U), Nco I (3.5 U), Eco RV (45.5 U), Stu I (7.9 U), Nar I (5 U), Nru I (6 U), Bcl I (18.2 U), Pvu I (4.5 U) and Dpn I (9.1 U) [Cla I, Eco RV, Sph I, Pvu I, Apa I, Sac I, Bgl I, Bcl I and Dpn I were the products of Boehringer Mannheim Company; Ava I, Xba I and Mbo I were the products of Bethesda Research Laboratories; Nco I and Xmn I were the products of New England Biolabs Inc.; Ban II was the product of Toyobo Co., Ltd.; Bam HI, Kpn I, Pst I, Pvu II, Xho I and Stu I were the products of Takara Shuzo Co., Ltd.]. The DNA was digested at 37 C for more than 4 hours.

When the DNA was digested with two restriction enzymes, first an enzyme for lower salt concentrations was added, and the hydrolysis was carried out at 37° C. for 4 hours at a salt concentration suitable for this enzyme. Then, the salt concentration was adjusted to one suitable for an enzyme for higher salt concentrations, and the enzyme for higher salt concentrations was added. The hydrolysis was further carried out at 37° C. for 4 hours. After the hydrolysis, 8 microliters of a solution containing 0.25% of bromophenol blue, 50% of glycerol and 10% of SDS was added, and the mixture was heat-treated at 65° C. for 5 minutes. The heat-treated mixture was subjected to 1.5% agarose gel electrophoresis. The agarose used was type II for electrophoresis made by Sigma Company. An aqueous solution of 40 mM Tris-acetate and 2 mM EDTA (pH 8.0) was used as a buffer for electrophoresis. Electrophoresis was carried out on a 5 mm-thick horizontal gel at a voltage of 1.5 V/cm for 11 to 15 hours. At the time of electrophoresis, a product obtained by completely digesting 0.5 microgram of lambda-DNA with Eco RI and Hind III and a product obtained by completely digesting 0.2 microgram of pBR322 DNA with Taq I were used as size markers for DNA fragments. After the electrophoresis, the agarose gel was withdrawn, dried on a gel drying plate, and subjected to autoradiography by the procedure described at pages 470 to 472 of the Manual of Maniatis et al. described hereinabove. The sizes of the resulting DNA fragments are as shown in Table 1 given hereinabove.

DNA fragments which appeared high in density for their sizes when observed after autoradiography are classified as dsDNA-a and those which appeared low in density for their sizes, as dsDNA-b.

Figure 3A:
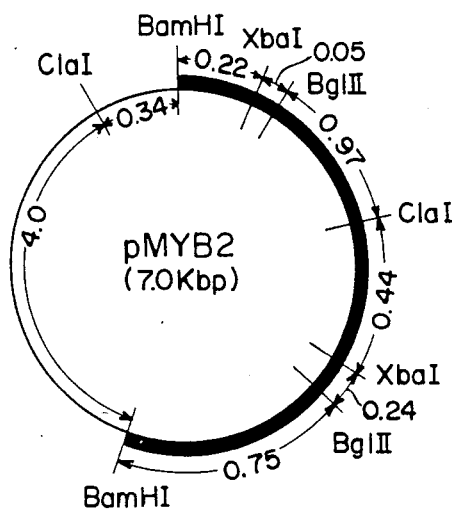
FIGS. 3(*a*) and 3(*b*), respectively, show hybrid DNAs pMYB2 and pMYB4 formed by the insertion of the Bam HI cleavage product of dsDNA TMM-1 into the Bam HI site of pBR322 in opposite directions.
Figure 3B:
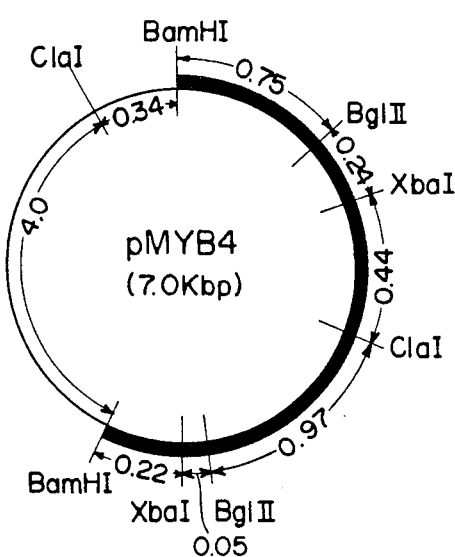

The parenthesized FIG. 3.3 shows that the DNA is open circular, and has an apparent molecular size of 3.3 Kbp with respect to the linear DNA size marker. It is presumed from this table that DNA which forms the fragments of dsDNA-a was open-circular and had a size of about 2.67 Kbp before digestion with restriction enzymes. The correct size can be known by determining the base sequences. But by methods available at present, a measuring error of 0.05 Kbp at the least cannot be avoided. The size of DNA which forms the fragments of dsDNA-a can be regarded as about 2.67±0.1 Kbp. From a similar analysis, DNA which produces the fragments of dsDNA-b can be regarded as being open-circular and having a size of 2.70±0.1 Kbp before digestion with restriction enzymes.

The relative positions of the sites of cleavage with various restriction enzymes were determined by digesting DNA with various enzymes either singly or in a combination of two and analyzing the cleavage patterns. FIG. 1 was obtained as a restriction enzyme cleavage map with regard to intact DNA which produced the fragments of dsDNA-a. FIG. 2 was obtained as a restriction enzyme cleavage map with regard to intact DNA which produced the fragments of dsDNA-b.

Ie. Hybrid DNA from the Bam HI diqestion product of the double-stranded DNA and pladmid pBR322 for E. coli A portion (50 microliters) taken from 100 microliters of the solution of double-stranded DNA obtained in experiment Ic above was subjected to gel filtration on a column (diameter 10 mm, length 10 cm) filled with Biogel P30 equilibrated with an aqueous solution of 10 mM Tris-HCl (pH 7.4) and 100 mM NaCl. Using an aqueous solution of 10 mM Tris-HCl (pH 7.4) and 100 mM NaCl as an eluent, ten drop (about 400 microliters) fractions were collected. A peak having a high $^{32}P$ count was observed in fractions Nos. 4 to 6. When the optical densities, $OD_{260}$, of the fractions were measured, it was found that the OD value began to increase with fraction No. 4, became a large value in fraction No. 9 and remained a large value in fractions No. 5 through No. 16. Fractions Nos. 4 to 6 which contained the double-stranded DNA were collected (1.2 ml), and 120 microliters of a 3M aqueous solution of sodium acetate (pH 5.4) and 3 ml of ethanol were added. The mixture was maintained at $-20°$ C. for 2 hours, and then centrifuged at 30,000 rpm for 30 minutes by a Beckman ultracentrifuge SW 50.1 rotor. The supernatant was discarded, and 5 ml of 75% ethanol kept at $-20°$ C. was freshly added. The mixture was centrifuged at 20,000 rpm for 2 minutes. The supernatant was discarded to form DNA pellets. The DNA pellets were dried in vacuum at 2 mmHg for 2 minutes, and dissolved in 50 microliters of distilled water. To 50 microliters of this DNA solution were added 6 microliters of a buffer for Bam HI (described in experiment Ic) and 6 microliters of Bam HI. THe reaction was carried out at 37° C. for 4 hours. Then, 10 microliters of a solution of yeast tRNA (2 microgram/microliter) and 70 microliters of distilled water were added. Furthermore, 100 microliters of water-saturated phenol was added. The mixture was shaken and centrifuged. The aqueous layer was taken out, and extracted with ether three times to remove the phenol.

Ten microliters of 3M sodium acetate (pH 4.8) and 350 microliters of ethanol were added. The mixture was left to stand at $-20°$ C. for 4 hours, and then centrifuged at a high speed. The resulting DNA pellets were dried and then dissolved in 17 microliters of distilled water.

To the solution were added 1 microliter of a solution (DNA 1 microgram/microliter) of the Bam HI-digested/alkaline phosphatase-treated product of pBR322, 2 microliters of a DNA ligation buffer [an aqueous solution containing 650 mM Tris-HCl (pH 7.4), 65 mM $MgCl_2$, 10 mM DTT, 5 mM ATP and 40 mM Spermine) and 0.5 microliter of T4-DNA ligase (1.2 units/microliter; Code No. 2010B of Takara Shuzo Co., Ltd.). The reaction was carried out at 14° C. for 22 hours. Then, the reaction mixture was treated at 65° C. for 5 minutes to obtain a hybrid DNA.

Using the hybrid DNA, competent cells of *E. coli* HB101 were transformed.

Preparation of the Bam HI-digested/alkaline phosphatase-treated product of pBR322

To 340 microliters of an aqueous solution containing 50 micrograms of plasmid pBR 322 DNA were added 40 microliters of the aforesaid restriction enzyme buffer for Bam HI and 20 microliters of Bam HI. They were reacted at 37° C. for 10 hours. Then, 44 microliters of 1M Tris-HCl (pH 8.0) was added. Furthermore, 10 microliters of bacterial alkaline phosphatase (BAP) [(0.4 U/microliter) made by Worthington Company] was added, and the mixture was treated at 65° C. for 7 hours. This reaction resulted in dephosphorylation of the 5' terminal of DNA. The reaction mixture was treated with 400 microliters of water-saturated phenol to remove proteins. It was further treated with 400 microliters of a mixture of phenol and chloroform (4:1 by volume) to remove proteins further. Finally, the aqueous solution was treated three times with 600 microliters of ether to extract the phenol component.

To 350 microliters of the aqueous layer were added 30 microliters of 3M sodium acetate and 1100 microliters of ethanol. The mixture was left to stand at $-20°$ C. for 2 hours, and centrifuged at a high speed. The resulting DNA pellets were dried, and dissolved in 50 microliters of distilled water. The solution was the solution (DNA 1 microgram/microliter) of the Bam HI-digested/alkaline phosphatase-treated product of pBR322.

Preparation and transformation of competent cells of E.coli HB101

A single colony of E. coli HB101 was transferred to 5 ml of L-broth medium, and cultivated with shaking at 37° C. for 11 hours. Two milliliters of the culture broth was inoculated in 200 ml of fresh L-broth, and cultivated with shaking at 37° C. for 2 hours and 20 minutes. When the $OD_{600}$ of the culture broth became 0.40, the culture broth was cooled to 0° C. and centrifuged at 5,000 rpm for 5 minutes by a Tomy cooling high-speed centrifuge (No. 9 rotor). The supernatant was discarded. The precipitated E. coli was homogenized in 50 ml of 10 mM aqueous NaCl solution, and again centrifuged at a high speed (No. 4 rotor; at 5,000 rpm for 5 minutes) to precipitate the bacterial cells. To the bacterial pellets was added 60 ml of 30 mM aqueous CaCl$_2$ solution. The mixture was homogenized and maintained at 0° C. for 20 minutes.

The homogenate was centrifuged at a high speed (No. 4 rotor; 4,000 rpm for 5 minutes at 4° C.). The supernatant was discarded, and 10 ml of an aqueous solution of 30 mM CaCl$_2$ and 15% glycerol was added to the bacterial pellets. The entire mixture was gently homogenized, and poured into 1.5 ml Eppendorf tubes as 200 microliter portions. They were stored in the frozen state at −80° C. The E. coli HB 101 cells treated with CaCl$_2$ were called competent cells.

The competent cells were transformed. Specifically, the competent cells were brought to a temperature of 0° C., and about 10 minutes later, the aqueous solution of the hybrid DNA prepared above was added. The mixture was maintained at 0° C. for 40 minutes and then heated at 42° C. for 2 minutes. Then, 1.2 ml of L-broth was added, and the mixture was maintained at 37° C. for 1 hour. The culture fluid was spread over eight L-agar plates (diameter 9 cm) containing 50 micrograms/ml of ampicillin at a rate of about 200 microliters per plate. The plates were maintained at 37° C. for 16 hours to obtain 86 colonies of transformed HB101. These 86 colonies were transferred to an L-agar plate containing 50 micrograms/ml of ampicillin and an L-agar plate containing 25 micrograms/ml of tetracycline at corresponding positions, and the two plates were incubated at 37° C. for 8 hours. As a result, 51 colonies were selected which were ampicillin-resistant and tetracycline-sensitive. By the boiling lysis method described at page 368 of the above-cited Manual of Miniatis et al., a mini-preparation of plasmid DNA was carried out on 15 colonies out of the 51 colonies, and then the plasmid DNA was digested with Bam HI. Plasmid fragments having a size of 2.67 Kbp, 2.02 Kbp and 0.67 Kbp were obtained. The fragment having a size of 2.67 Kbp was obtained by cleavage of dsDNA-a with Bam HI, and the fragments having sizes of 2.02 and 0.67 Kbp were presumably derived from two kinds of fragments generated by the digestion of dsDNA-b with Bam HI. A hybrid DNA of the fragment having a size of 2.67 Kbp and pBR322 is designated as pMYB4; a hybrid DNA of the fragment having a size of 2.02 Kbp and pBR322, as pMYB5; and a hybrid DNA of the fragment having a size of 0.67 Kbp and pBR322, as pMYB3. The DNAs of pMYB4, pMYB3 and pMYB5 were obtained by replication and propagation in the host E. coli of pBR322 and were in the completely double-stranded state.

The hybrid DNA pMYB4 was completely digested with Bam HI, Bam HI/Bgl II, Bam HI/Bgl II/Cla I, Bam HI/Xba I, and Bam HI/Xba I/Bgl II, and subjected to 1.2% agarose gel electrophoresis (the digestion product of lambda-DNA with Eco RI/Hind III and the digestion product of pBR322 with Taq I were also subjected to electrophoresis as size markers). The fragment sizes of DNA were analyzed, and the results shown in Table 3 were obtained.

The hybrid DNA pMYB5 was digested with Bam HI, Bam HI/Hind III/Bgl II and Bam HI/Hind III/Pst I, and the hybrid DNA pMYB3 was digested with Bam HI and Bam HI/Hind III. The same analysis as above was carried out. The results shown in Table 3 were obtained.

TABLE 3

| Hybrid DNA | Restriction enzyme | DNA fragment size (Kbp) |
|---|---|---|
| pMYB4 | Bam HI | (4.3), 2.67 |
| | Bam HI/Bgl II | (4.3), 1.67, 0.74, 0.32 |
| | Bam HI/Bgl II/Cla I | (4.0), 0.94, 0.74, 0.68, (0.36), 0.30 |
| | Bam HI/Xba I | (4.3), 1.46, 0.97, 0.21 |
| | Bam HI/Xba I/Bgl II | (4.3), 1.37, 0.74, 0.21–0.25 (*), 0.05–0.10 |
| pMYB5 | Bam HI | (4.3), 2.02 |
| | Bam HI/Hind III/Bgl II | (4.0), 0.96, 0.78, (0.35) 0.32 |
| | Bam HI/Hind III/Pst I | (3.2), 0.96, (0.78) 0.73, (0.35), 0.34 |
| pMYB3 | Bam HI | (4.3), 0.67 |
| | Bam HI/Hind III | (4.0), 0.67, (0.35) |

The parenthesized figures are for DNAs derived from pBR322.
(*): There were two DNA bands between 0.21 and 0.25.

The sizes of the fragments formed by the digestion of pMYB4 with the restriction enzymes shown in Table 3 contained measurement errors of a maximum of about ±0.1 Kbp.

In this experiment, another kind of a hybrid DNA having the Bam HI fragment witha a size of 2.67 Kbp at the Bam HI site of pBR322 is designated as pMYB2. Digestion of pMYB4 with Cla I gave fragments having a size of 5.4 and 1.6 Kbp. Digestion of pMYB4 with Cla I gave fragments having a size of 5.2 and 1.8 Kbp.

The Bam HI fragments having a size of 2.67 Kbp were taken out from pMYB4 and pMYB2 by the method described hereinbelow. Digestion of the fragments with Bgl II gave three fragments having a size of 1.67, 0.74 and 0.3 Kbp from each of the 2.67 Kbp fragments. Digestion of the 2.67 Kbp fragments with Cla I gave fragments having a size of 1.42 and 1.24 Kbp, respectively.

It is seen from the foregoing results that pMYB4 and pMYB2 are hybrid DNAs which were formed by the insertion of the Bam HI cleavage product of dsDNA TMM-1 into the Bam HI site of pBR322 in opposite directions as shown in FIGS. 3-(a) and 3-(b).

If. Hybrid DNA of the Hind III digestion product of the double-stranded DNA and E. coli plasmid pBR322

Substantailly the same operation as in experiment Ie was carried out except that the double-stranded DNA and pBR322 were digested with Hind III instead of Bam HI (the salt concentration was lowered to suit the digestion with Hind III. A solution of the double-stranded DNA digested with Hind III in 17 microliters of sterilized water, 1 microliter of a solution (DNA 1 microgram/microliter) of the Hind III-digested/alkaline phosphatase-treated product of pBR322, 2 microliters of the aforesaid buffer for DNA ligase and 0.5 microliter of T4 DNA ligase were reacted at 14° C. for 22 hours to obtain a hybrid DNA in the same way as in experiment Ie. Using the hybrid DNA, competent cells of E. coli HB101 were transformed by the same operation as in experiment Ie to obtain 37 transformants. A mini-preparation of plasmid DNA was carried out by the boiling lysis method in the same way as in Ie on 15 colonies out of the 37 colonies, and the plasmid DNA was digested with Hind III. Plasmids containing a fragment with a size of 2.70 Kbp were obtained (one of the hybrid plasmid DNAs was designated as pMYH3). pMYH3 was a hybrid DNA containing the whole of dsDNA-b. The hybrid DNA pMYH3 was obtained by replication and propagation in E. coli and was in the completely double-stranded state.

The hybrid DNA pMYH3 was digested with Hind III, Hind III/Bam HI, Hind III/Pst I and Hind III/Bam HI/Bgl II, and the resulting fragments were analyzed in the same way as in experiment Ie. The sizes of the fragments obtained are shown in Table 4.

TABLE 4

| Restriction enzyme | DNA fragment size (Kbp) |
| --- | --- |
| Hind III | (4.3), 2.69 |
| Hind III/Bam HI | (4.0), 1.04, 0.96, 0.68, (0.30) |
| Hind III/Pst I | (3.6), 2.35, (0.78), 0.35 |
| Hind III/Bam HI/Bgl II | (4.0), 0.96, 0.78, 0.68, (0.35), 0.32 |

The parenthesized figures are for DNAs derived from pBR322.

The sizes of the DNA fragments formed by the digestion of pMYH3 with the various enzymes shown in Table 4 had a measurement error of a maximum of about ±0.1 Kbp.

The fragment sizes well agreed with those which can be presumed from the restriction enzyme cleavage patterns shown in Table 1.

In this experiment, another hybrid DNA having a Hind III-digested fragment with a size of 2.70 Kbp at the Hind III site of pBR322 was designated as pMYH14.

Digestion of pMYH3 with Pst I gave fragments having a size of 5.9 and 1.1 Kbp. Digestion of pMYH14 with Pst I gave fragments having a size of 3.9 and 3.1 Kbp.

Hind III-digested fragments having a size of 2.70 Kbp were taken out from pMYH3 and pMYH14 by the method described hereinbelow, and digested with Bam HI. Fragments having a size of 1.10, 0.96 and 0.67 Kbp were formed from each of the 2.70 Kbp fragments. Digestion with Bgl II gave fragments having a size of 1.92 and 0.78 Kbp from each of the 2.70 Kbp fragments.

Figure 4A:
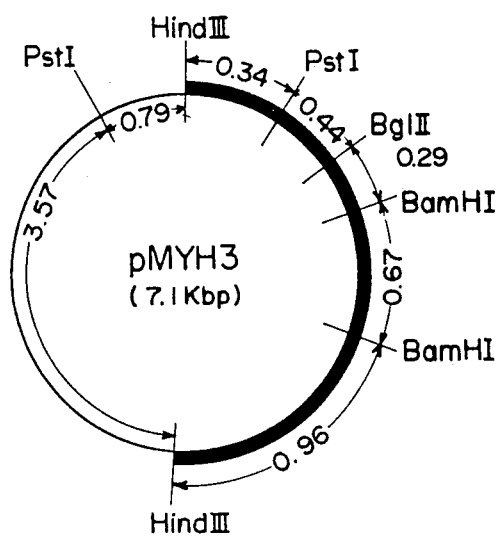
FIGS. 4(*a*) and 4(*b*) represent hybrid DNAs pMYH3 and pMYH14 formed by the insertion of Hind III-cleaved dsDNA TMM-2 into the Hind III site of pBR322 in opposite directions.
Figure 4B:
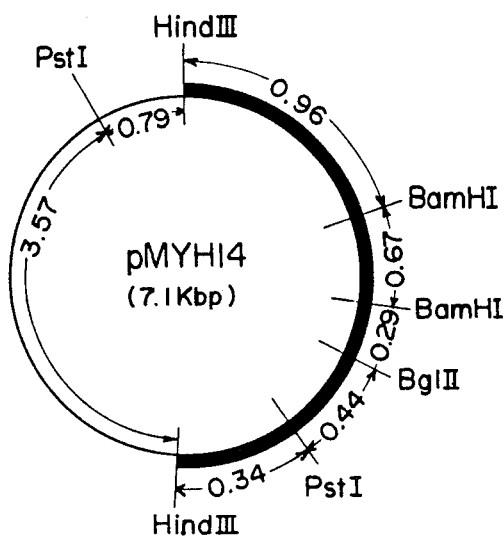

It was found therefore that pMYH3 and pMYH14 are hybrid DNAs formed by the insertion of Hind III-cleaved dsDNA TMM−2 into the Hind III site of pBR322 in opposite directions, as shown in FIGS. 4-(a) and -(b).

The hybrid DNA pMYB2, pMYB4, pMYH3 and pMYH14 obtained in the experiments Ie and If are hybrid DNAs of dsDNA Tmm-1 and dsDNA Tmm-2 and pBR322. They can also be vectors for plant gene recombination.

Ig. Separation of dsDNA Tmm-1 and dsDNA Tmm-2 from the hybrid DNA pMYB4 and pMYH3 and ligation thereof Twenty micrograms of each of pMYB4 and pMYH3 was hydrolyzed at 37° C. for 10 hours using 20 units of Bam HI and 20 units of Hind II respectively and the aforesaid restriction enzyme reaction buffers (for adjusting the salt concentration) (the total amount of the reaction mixture was 400 microliters). The product was subjected to electrophoresis at 1 V/cm for 10 hours using 0.8% agarose gel (well width 1.5 mm; length 6 cm; depth 7 mm; gel length 13 cm). The gel slice having fragments with a size of 2.67 Kbp or 2.70 Kbp was cut off. DNAs were extracted from it by the method described at pages 164 to 165 of the aforesaid Manual of Maniatis et al., and then purified by the method described at page 166 of the same Manual. The purified DNAs were each dissolved in 50 microliters of sterilized water (DNA about 0.1 microgram/microliter). To 20 microliters of each DNA aqueous solution were added 5 microliters of the aforesaid DNA ligation buffer, 25 microliters of sterilized water and 0.5 microliter of T4-DNA ligase, and they were reacted at 12° C. for 19 hours. The product was subjected to 0.8% agarose gel electrophoresis in the same way as above. The gel slice having a DNA band portion with an apparent size of 3.3 Kbp was cut off, and the DNA was extracted and purified in the same way as above. It is assumed that the DNAs so purified were circular dsDNA Tmm-1 and Tmm-2.

Sterilized water (10 microliters) was added to each of the DNAs, and a 2 microliter portion of the solution was subjected to partial digestion with Bam HI or Hind III. The partial digestion was carried out by adding 5 microliters of the aforesaid restriction enzyme reaction buffer, 43 microliters of sterilized water and 0.5 unit of Bam HI (for dsDNA Tmm-1) or 0.5 unit of Hind III (for dsDNA Tmm-2) to 2 microliters of the DNA solution, and reacting them at 37° C. for 5, 10 and 30 minutes respectively. Each of the reaction products was subjected to 0.8% agarose gel electrophoresis and changes in size were examined. The band with an apparent size of 3.3 Kbp gradually decreased and bands of linear DNA fragments having a size of 2.67 and 2.70 Kbp of dsDNA Tmm-1 and Tmm-2 increased as the reaction time became longer. No other band was observed. It can be concluded therefore that the above circular DNAs were monomers and dsDNA Tmm-1 and Tmm-2. These DNAs were in the completely double-stranded state. They can be used as vectors in plant gene recombination.

The dsDNA Tmm-1 and dsDNA Tmm-2 so obtained were each digested with the enzymes indicated in Tables 5 and 6. Digestion was carried out at 37° C. for 2 to 4 hours using 0.4 microgram of each DNA, the restriction enzyme reaction buffer and 4 to 8 units of each restriction enzyme. After complete digestion, the product was subjected to 1.5% agarose gel electrophoresis in the same way as in Id. The gel was stained with ethidium bromide and irradiated with $UV_{254}$ nm to detect DNA bands. The DNA fragments formed by digestion had the sizes shown in Tables 5 and 6.

During the agarose gel electrophoresis, the Eco RI/Hind III digestion product of lambda-DNA and the Taq I digestion product of pBR322 DNA were used as size markers for DNA as in Id.

In the following Tables, the fragment sizes with Dpn I were those of fragments which could be detected. Not all fragments with Dpn I could be detected since they were large in number and small in size.

TABLE 5

| Restriction enzyme | Fragment DNA size (Kbp) |
| --- | --- |
| Bam HI | 2.68 |
| Bgl II | 1.66, 1.03 |
| Xba I | 1.47, 1.20 |
| Cla I | 2.67 |
| Xmn I | 2.68 |
| Nar I | 2.66 |
| Nco I | 2.67 |
| Ava I | 2.65 |
| Bgl II | 1.65, 1.04 |
| Dpn I | 0.95, 0.46, 0.32, 0.31, 0.19, 0.19, 0.18, 0.08 |
| Bam HI/Xba I | 1.48, 0.97, 0.22 |
| Bam HI/Bgl II | 1.66, 0.74, 0.31 |
| Bgl II/Xba I | 1.35, 0.96, 0.22  ca. 0.05 |
| Cla I/Bgl II | 1.03, 0.98, 0.67 |

TABLE 5-continued

| Restriction enzyme | Fragment DNA size (Kbp) |
| --- | --- |
| Cla I/Xba I | 1.19, 1.03, 0.45 |
| Xmn I/Bam HI | 1.71, 0.97 |
| Xmn I/Nar I | 1.66, 1.02 |
| Nar I/Bgm HI | 2.63 ca. 0.05 |
| Ava I/Bam HI | 1.23, 1.43 |
| Ava I/Bgl II | 1.03, 0.98, 0.68 |
| Not digestible with Kpn I, Mlu I, Pvu II, Pvu I, Sal I, Xho I, Hind III, Pst I, Sac I, Sph I, Eco RV, Stu I, Nru I, Bcl I, Ban II, Apa I, Hpa I and Mbo I | |

TABLE 6

| Restriction enzyme | Fragment DNA size (Kbp) |
| --- | --- |
| Bam HI | 2.04, 0.69 |
| Bgl II | 2.71 |
| Pst I | 2.72 |
| Hind III | 2.68 |
| Xmn I | 1.93, 0.77 |
| Nar I | 2.70 |
| Hpa I | 2.69 |
| Nco I | 2.70 |
| Dpn I | 0.51, 0.46, 0.26, 0.23*[1], 0.21, 0.20, 0.12, 0.12, 0.06*[2], 0.04 |
| Bgl II/Pst I | 2.29, 0.45 |
| Bam HI/Pst I | 1.28, 0.75, 0.71 |
| Bam HI/Bgl II | 1.73, 0.71, 0.29 |
| Hind III/Bgl II | 1.95, 0.75 |
| Hind III/Bam HI | 1.07, 0.96, 0.67 |
| Xmn I/Bam HI | 1.61, 0.43, 0.36, 0.32 |
| Xmn I/Nar I | 1.33, 0.77, 0.61 |
| Hind III/Xmn I | 1.30, 0.77, 0.65 |
| Hpa I/Nco I | 1.36, 1.34 |
| Hpa I/Hind III | 2.51 ca. 0.05 |
| Hind III/Nco I | 1.54, 1.17 |
| Not digestible with Kpn I, Cla I, Xba I, Sac I, Bgl I, Sph I, Eco RV, Stu I, Nru I, Bcl I, Ava I, Apa I and Mbo I | |

[*1; may be triplet,
*2; triplet]

Ih. Extraction of MYMV replicative DNA from MYMV-infected plant and its analysis Forty milliliters of 0.5M $KH_2PO_4$/0.75% $Na_2SO_3$ (pH 7.0) was added to 20 g of MYMV-infected leaves of Top Crop, and the mixture was ground uniformly in a mortar with a pestle. Then, 1.2 ml of Triton X-100 was added, and the mixture was stirred at 4° C. for 12 hours. The mixture was then filtered on a double-layer gauze. The filtrate was centrifuged at 7,000 rpm for 15 minutes in a Tomy No. 4 rotor. The supernatant was separated and centrifuged at 32,000 rpm for 4.5 hours by a Beckman ultracentrifuge (type SW 40.1 rotor). The supernatant was discarded. To the precipitated pellets were added 1 ml of 40 mM Tris-HCl, 5 mM acetic acid and 10 mM EDTA (pH 8.2), and they were homogenized. Then, 20 microliters of 10% SDS was added. The mixture was extracted three times with 1 ml of water-saturated phenol and then three times with 1 ml of phenol/chloroform (4/1) to remove proteins, etc. from the aqueous layer. The residue was extracted four times with 1 ml of ether to remove phenol. To the aqueous layer were added 100 microliters of 3M sodium acetate and 3 ml of ethanol. The mixture was left to stand at −20° C. for 5 hours, and then centrifuged at a high speed to sediment DNA pellets. To the DNA pellets was added 500 microliters of sterilized water (DNA concentration 0.47 microgram/microliter). One hundred microliter of the resulting DNA solution was subjected to 0.8% agarose gel electrophoresis by the same technique as in experiment Ig. DNA corresponding to a band with an apparent size of 1.6 Kbp, DNA corresponding to a band with an apparent size of 3.2 Kbp, DNA corresponding to a band with an apparent size of 5.4 Kbp and DNA corresponding to a band with an apparent size of 10 Kbp which were hybridized with $^{32}P$-labelled DNA probe (the $^{32}P$-labelled probe is described in experiment Ii) of MYMV were taken out from the gel and purified by the same technique as in Ig. (Portions of the gel corresponding to bands with an apparent size of 5.4 Kbp and 10 Kbp were cut off by using the Eco RI/Hind III digestion product of lambda-DNA as a size marker.)

The four DNAs were each digested with Bam HI, Bgl II and Bgl II/Pst I, and then subjected to agarose gel electrophoresis. The digestion patterns were analyzed. With regard to the DNAs corresponding to 5.4 Kbp and 10.0 Kbp, the digested DNAs were transferred to a nitrocellulose filter after agarose gel electrophoresis, and by using the $^{32}P$-labelled DNA of MYMV, DNA-DNA hybridization and autoradiography were carried out. Then, the digestion patterns of the DNAs were analyzed. The digestion patterns were 2.66, 2.01 and 0.62 Kbp by digestion with Bam HI, 2.71, 1.64 and 1.04 Kbp by digestion with Bgl II, and 2.27, 1.67, 1.02 and 0.44 Kbp by double digestion with Bgl II/Pst I. These are the same as the digestion patterns of dsDNA-a and dsDNA-b with these restriction enzymes. This means that these replicative DNAs contain DNA-a or DNA-b and can be used as vectors for plant gene recombination.

Ii. Preparation of a hybrid DNA from replicative DNA and pBR322

To the replicative DNA (9 microgram/10 microliters) extracted in experiment Ih from the agarose gel at a band portion corresponding to an apparent size of 1.6 Kbp were added 4 microliters of the aforesaid restriction enzyme buffer for Hind III, 24 microliters of sterilized water and 3 microliters of Hind III, and the DNA was hydrolyzed at 37° C. for 2 hours. Sterilized water (65 microliters) and 20 micrograms of yeast tRNA were added to the product, and the mixture was treated with two 100 microliter portions of water-saturated phenol to remove proteins. The aqueous layer was extracted four times with 150 microliters of ether to remove phenol. Then, 10 microliters of 3M sodium acetate (pH 4.8) and 300 microliters of ethanol were added. The mixture was left to stand at −20° C. for 2 hours, and then centrifuged at a high speed to form a precipitate. The precipitate was washed with 500 microliters of cold 70% ethanol, and centrifuged again. The supernatant was discarded, and the precipitate was dried at 2 mmHg for 3 minutes. The precipitate was dissolved in 10 microliters of sterilized water. This solution is named Hind III-digested product of replicative DNA. To 6 microliters (DNA about 0.2 micrograms) of the Hind III digestion product were added 4 microliters of the same Hind III-digested/alkaline phosphatase-treated product of pBR322 (DNA 1 microgram/microliter) as used in experiment If, 2 microliters of the aforesaid DNA ligation buffer, 0.5 microliter of T4 DNA ligase and 7.5 microliters of sterilized water, and they were reacted at 14° C. for 13 hours. The product was then treated at 65° C. for 5 minutes. Using the resulting hybrid DNA, the competent cells of E. coli HB101 were transformed by the same operation as in experiment If to obtain about 130 transformants. A nitrocellulose filter (BA85 manufactured by Schleicher und Schüll Company; this is the same as the nitrocellulose filter as described hereinabove) was placed on an L-agar plate in which the colonies of the transformants formed. Then, the nitrocellulose filter was removed, and dipped for 1 minute in 0.5M sodium hydroxide and 1.5M sodium chloride and then in 1M Tris-HCl (pH 7.0). The nitrocellulose filter was then heat-treated at 80° C. and 1 mmHg for 2 hours. The heat-treated filter was dipped in a prehybridization solution [consisting of 0.9M NaCl, 0.09M sodium citrate, 0.02% polyvinyl pyrrolidone (Plasdone NP K-30, a product of Wako Pure Chemicals, Co., Ltd.), 0.02% Ficoll (Ficoll 400 prepared by Pharmacia Fine Chemicals), and 0.02% aqueous solution of bovine serum aluminum] and pre-treated at 63° C. for 30 minutes. Then, the prehybridization solution was removed, and a hybridization solution prepared by adding SDS (final 2%) and yeast tRNA (final 40 micrograms/ml) to the prehybridization solution and $200 \times 10^4$ cpm of $^{32}P$ probe of MYMV described below were added. The nitrocellulose filter treated as above was put in this solution, and DNA-DNA hybridization was carried out at 63° C. for 24 hours. The filter was then taken out, and shaken slowly at 55° C. for 20 minutes in large amounts of 0.45M NaCl and 0.045M sodium citrate. This washing was carried out three times. The filter was then dried, and autoradiography was carried out by the same technique as described at pages 470 to 472 of the aforesaid manual of Maniatis et al. About 8 colonies were observed which were hybridized with $^{32}P$-labelled DNA of MYMV.

Preparation of $^{32}P$ probe of MYMV

Experiment Ic was repeated except that 10 microliters of 0.8 mM deoxycytidine triphosphate was not used. Gel filtration on Sephadex G-75 was carried out. The first $^{32}P$ peak (total $300 \times 10^4$ cpm) appeared in fractions Nos. 6 to 11. These fractions were collected (total 800 microliters), heated at 95° C. for 5 minutes, and then rapidly cooled to 0° C. The resulting solution was used as a $^{32}P$-labelled DNA probe of MYMV.

With regard to the 8 colonies mentioned above, a mini-preparation of a plasmid DNA was carried out by the boiling lysis method described above, and the plasmid DNA was digested with Hind III. There were obtained hybrid plasmids containing a fragment with a size of 2.70 Kbp from six colonies. One of these hybrid DNAs was designated as pMYRFH1.

When pMYRFH1 was digested with Bam HI/Hind III and Hind III/Bam HI/Bgl II, the same DNA fragments as shown in Table 4 were obtained.

Ij. Preparation of a hybrid DNA from replicative DNA and pBR322

DNA extracted from a band portion having an apparent size of 3.2 Kbp in experiment Ih was digested with Bam HI, and treated with the same Bam HI-digested-/alkaline phosphatase-treated product of pBR322 as in experiment Ie to obtain a hybrid DNA. E. coli was transformed with the resulting hybrid DNA. Plasmids were extracted from the transformants obtained in the same way as in experiment Ie, and analyzed in the same way as in experiment Ie. In this manner, hybrid DNAs, pMYRFB1, pMYRFB3 and pMYRFB4, containing Bam HI-digested fragments having a size of 2.68, 2.03 and 0.68 Kbp at the Bam HI site of pBR322 were obtained as in experiment Ie.

When pMYRFB1 was digested with Bam HI/Bgl II and Bam HI/Xba I, the same DNA fragments as in Table 3 were formed. It can be concluded from the results of experiments Ii and Ij that the present replicative DNAs contain dsDNA-a and -b. Further it can be concluded that pMYRFH1 is a hybrid DNA from dsDNA-b- and pBR322 and pMYRFB1, from dsDNA-a and pBR322. By using the technique of this experiment, dsDNA-a and dsDNA-b can be individually separated, and propagated.

Ik. Hybrid DNA of the Bam HI digestion product of the double-stranded DNA and E. coli plasmid pBR328

The double-stranded DNA of MYMV was prepared in the same way as in experiment Ic.

Substantially the same operation as in experiment Ie was carried out except that the plasmid pBR328 was digested with Bam HI instead of digesting pBR322.

A solution of the double-stranded DNA digested with Bam HI in 17 microliters of sterilized water, 1 microliter of a solution (DNA 1 microgram/microliter) of the Bam HI-digested/alkaline phosphatase-treated product of pBR328 (prepared as in the preparation of Bam HI-digested/alkaline phosphatase-treated product of pBR322 in experiment Ie), 2 microliters of the aforesaid buffer for DNA ligase and 0.5 microliter of T4 DNA ligase were reacted at 14° C. for 18 hours to obtain a hybrid DNA in the same way as in experiment Ie. Using the hybrid DNA, competent cells of E. coli HB101 were transformed by the same operation as in experiment Ie to obtain 22 transformants. A mini-preparation of plasmid DNA was carried out on the 22 colonies by the alkaline lysis method described at pages p368 to p369 of the aforesaid manual of Maniatis et al., and the plasmid DNA was digested with Bam HI. Plasmids containing a fragment with a size of 2.67 Kbp were obtained (two of the hybrid plasmid DNAs were designated as pMYB81 and pMYB82). The hybrid DNA pMYB81 and pMYB82 were obtained by replication and propagation in E. coli and were in the completely double-stranded state.

Digestion of pMYB81 with Cla I gave fragments having a size of 6.0 and 1.58 Kbp. Digestion of pMYB82 with Cla I gave fragments having a size of 5.8 and 1.77 Kbp.

Bam HI-digested fragments having a size of 2.67 Kbp were taken out from pMYB81 and pMYB82 by the aforesaid method, and digested with Cla I. Fragments having a size of 1.43 and 1.24 Kbp were formed from each of the 2.67 Kbp fragments.

Figure 5:
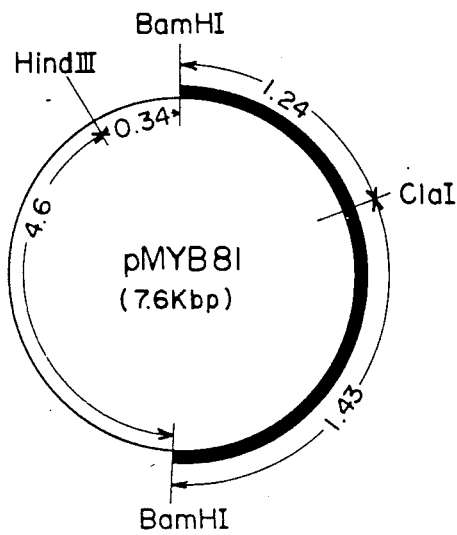
FIG. 5 shows the hybrid DNA pMYB 81 formed by the insertion of Bam HI-cleaved dsDNA TMM-1 into the Bam HI site of pBR322.

It was found therefore that pMYB81 and pMYB82 are hybrid DNAs formed by the insertion of Bam HI-cleaved dsDNA Tmm-1 into the Bam HI site of pBR328 in opposite directions. The hybrid DNA pMYB81 is shown in FIG. 5.

The hybrid DNAs pMYB81 and pMYB82 obtained in this experiment are hybrid DNAs of dsDNA Tmm-1 and pBR328. They can also be vectors for plant gene recombination.

Il. Hybrid DNA of the Pst I digestion product of the double-stranded DNA and E. coli plasmid pBR328

The double-stranded DNA of MYMV was prepared as in experiment Ic.

Substantially the same operation as in experiment Ie was carried out except that the double-stranded DNA and pBR328 were digested with Pst I instead of Bam HI (the salt concentration was lowered to suit the digestion with Pst I). A solution of the double-stranded DNA digested with Pst I in 17 microliters of sterilized water, 1 microliter of a solution (DNA 1 microgram/microliter) of the Pst I-digested/alkaline phosphatase-treated product of pBR325 (to be described below), 2 microliters of the aforesaid buffer for DNA ligase and 0.5 microliter of T4 DNA ligase were reacted at 14° C. for 20 hours to obtain a hybrid DNA in the same way as in experiment Ie.

Preparation of the Pst I-digested/alkaline phosphatase-treated product of pBR328

In the preparation of the Bam HI-digested/alkaline phosphatase-treated product of pBR322 described in experiment Ie, the same operation was carried out except that 20 microliters of Pst I was used instead of 20 microliters of Bam HI and pBR328 was used instead of pBR322. Finally 50 microliters (DNA concentration 1 microgram/microliter) of a solution of the Pst I-digested/alkaline phosphatase-treated product of pBR328 was prepared.

Using the hybrid DNA, competent cells of E. coli HB101 were transformed by the same operation as in experiment Ie except that 25 micrograms/ml of tetracycline was used instead of 50 micrograms/ml of ampicillin. Thus, 51 transformants were obtained. A mini-preparation of plasmid DNA was carried out on the 51 colonies by the alkaline lysis method as in experiment Ik, and the plasmid DNA was digested with Pst I. Eleven plasmids containing fragments with a size of 2.70 Kbp were obtained (two of the hybrid plasmid DNAs were designated as pMYP81 and pMYP82). pMYP81 and pMYP82 were hybrid DNAs containing the whole of dsDNA Tmm-2.

The hybrid DNAs pMYP81 and pMYP82 were obtained by replication and propagation in E. coli and were in the completely double-stranded state.

Digestion of pMYP81 with Bam HI gave fragments having a size of 4.10, 2.82 and 0.67 Kbp. Digestion of pMYP82 with Bam HI gave fragments having a size of 3.5, 3.4 and 0.67 Kbp.

A Pst I-digested fragment having a size of 2.70 Kbp was taken out from each of pMYP81 and pMYP82 by the aforesaid method, and digested with Bam HI. Fragments having a size of 1.30, 0.73 and 0.67 Kbp were formed.

Figure 6:
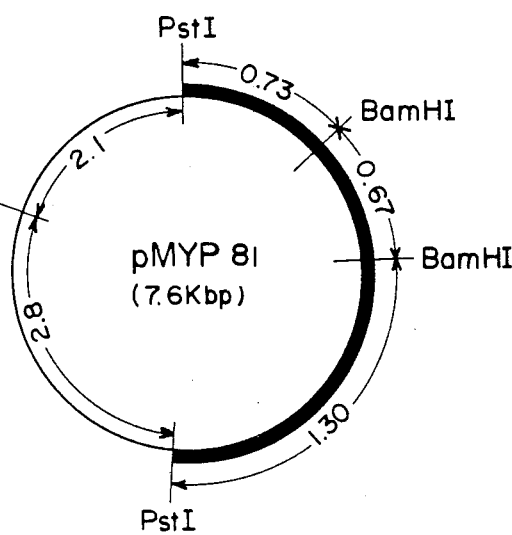
FIG. 6 shows the hybrid DNA pMYP81 formed by the insertion of PSt I-cleaved dsDNA TMM-2 into the Pst-I site of pBR328.

It was found therefore that pMYP81 and pMYP82 are hybrid DNAs formed by the insertion of Pst I-cleaved dsDNA Tmm-1 into the Pst I site of pBR328 in opposite directions. The hybrid DNA pMYP81 is shown in FIG. 6.

The hybrid DNAs pMYP81 and pMYP82 obtained in this experiment are hybrid DNAs of dsDNA Tmm-2 and pBR328. They can also be vectors for plant gene recombination.

Im. Preparaion of a hybrid DNA from replicative DNA and pBR325

DNA extracted from a band portion having an apparent size of 3.2 Kbp in experiment Ih was digested with Bam HI, and treated with the same Bam HI-digested/alkaline phosphatase-treated product of pBR325 (to be described below) as in experiment Ik to obtain a hybrid DNA.

Preparation of the Bam HI-digested/alkaline phosphatase-treated product of pBR325

In the preparation of the Bam HI-digested/alkaline phosphatase-treated product of pBR322 described in experiment Ie, the same operation was performed except that pBR325 was used instead of pBR322. Finally, 50 microliters (DNA 1 microgrfam/microliter) of a solution of the Bam HI-digested/alkaline phosphatase-treated product of pBR325 was prepared.

E. coli was transformed with the resulting hybrid DNA. Plasmids were extracted from 32 transformants obtained in the same way as in experiment Ik, and analyzed in the same way as in experiment Ie. In this manner, hybrid DNAs, pMYRFB51, pMYRFB52, pMYRFB53 and pMYRFB54, containing Bam HI-digested fragments having a size of 2.67, 2,67, 2.03 and 0.68 Kbp resectively at the Bam HI site of pBR325 were obtained as in experiment Ie.

When pMYRFB51 and pMYRFB52 were digested with Cla I, the former plasmid gave fragments having a size of 7.0 and 1.6 Kbp, and the latter plasmid gave fragments having a size of 6.8 and 1.8 Kbp.

When pMYRFB51 and pMYRFB52 were digested with Bam HI/ClaI, both of the plasmids gave the same DNA fragments having a size of (5.6), (0.3), 1.4 and 1.24 Kbp. (The parenthesized fragments are asigned to pBR325.)

It was found therefore that pMYRFB51 and pMYRFB52 are hybrid DNAs formed by the insertion of Bam HI-cleaved dsDNA-a into the Bam HI site of pBR325 in opposite directions.

These two hybrid DNAs can also be vectors for plant gene recombination.

In. Preparation of a hybrid DNA from replicative DNA and pBR325

Replicative DNA (same as in experiment Im; apparent size 3.2 Kbp) was digested with Pst I and ligated with the Pst I-digested/alkaline phosphatase-treated product of pBR325 (to be described below) as in experiment Il to obtain a hybrid DNA.

Preparation of the Pst I-digested/alkaline phosphatase-treated product of pBR325

In the preparation of the Bam HI-digested/alkaline phosphatase-treated product of pBR322 described in experiment Ie, the same operation was performed except that 20 microliters of Pst I was used instead of 20 microliters of Bam HI and pBR325 was used instead of pBR322. Finally, 50 microliters (DNA 1 microgram/microliter) of a solution of the Pst I-digested/alkaline phosphatase-treated product of pBR 325 was prepared.

E. coli HB101 was transformed with the hybrid DNAs. Plasmids were extracted from 17 transformants obtained as in experiment Il, and analyzed in the same way as in experiment Ie. In this manner, hybrid DNAs pMYRFP51 and pMYRFP52 having a size of 2.70 Kbp at the Pst I site of pBR325 were obtained.

When pMYRFP51 and pMYRFP52 were digested with Bam HI, the former plasmid gave a fragment set of 4.5, 3.4 and 0.67 Kbp and the latter plasmid gave a fragment set of 3.9, 4.0 and 0.67 Kbp.

When pMYRFP51 and pMYRFP52 were digested with Pst I/Bam HI, both of the pladmids gave the same DNA fragments having a size of (3.2), (2.7), 1.30, 0.73 and 0.67 Kbp. (The parenthesized fragments are assigned to pBR325.)

It was found therefore that pMYP51 and pMYP52 are hybrid DNAs formed by the insertion of Pst I-cleaved dsDNA-b into the Pst I site of pBR325 in opposite directions.

These two hybrid DNAs can also be vectors for plant gene recombination.

Io. Hvbrid DNA of the Cla I digestion product of the double-stranded DNA and E. coli plasmid pBR322

The double-stranded DNA of MYMV was prepared as in experiment Ic.

Substantially the same operation as in experiment Ie was carried out except that the double-stranded DNA and pBR 322 were digested with Cla I instead of Bam HI (the salt concentration was lowered to suit the digestion with Cla I). A solution of the double-stranded DNA digested with Cla I in 17 microliters of sterilized water, 1 microliter of a solution (DNA 1 microgram/microliter) of the Cla I-digested/alkaline phosphatase-treated product of pBR322 (to be described below), 2 microliters of the aforesaid buffer for DNA ligase and 0.5 microliter of T4 DNA ligase were reacted at 14° C. for 20 hours to obtain a hybrid DNA in the same way as in experiment Ie.

Preparation of the Cla I-digested/alkaline phosphatase-treated product of pBR322

In the preparation of the Bam HI-digested/alkaline phosphatase-treated product of pBR322 described in experiment Ie, the same operation was performed except that 20 microliters of Cla I was used instead of 20 microliters of Bam HI. Finally, 50 microliters (DNA concentration 1 microgram/microliter) of a solution of the Cla I-digested/alkaline phosphatase-treated product of pBR322 was prepared.

Using the hybrid DNA, competent cells of E. coli HB101 were transformed by the same operation as in experiment Ie to obtain 13 transformants. A mini-preparation of plasmid DNA was carried out on the 13 colonies by the boiling lysis method in the same way as in experiment Ie, and the plasmid DNA was digested with Cla I. Seven plasmids containing fragments with a size of 2.67 Kbp were obtained (two of the hybrid plasmid DNAs were designated as pMYC1 and pMYC2). pMYC1 and pMYC2 were hybrid DNAs containing the whole of dsDNA Tmm-1.

The hybrid DNA, pMYC1 and pMYC2 were obtained by replication and propagation in E. coli and were in the completely double-stranded state.

Digestion of pMYC1 with Bam HI gave fragments having a size of 5.25 and 1.78 Kbp. Digestion of pMYC2 with Bam HI gave fragments having a size of 5.44 and 1.59 Kbp.

A Cla I-digested fragment having a size of 2.67 Kbp was taken out from each of pMYC1 and pMYC2 by the aforesaid method, and digested with Bam HI. Fragments having a size of 1.43 and 1.24 Kbp were formed. Digestion with Bgl II gave fragments having a size of 1.04, 0.97 and 0.68 Kbp.

It was found therefore that pMYC1 and pMYC2 are hybrid DNAs formed by the insertion of Cla I-cleaved dsDNA Tmm-1 into the Cla I site of pBR322 in opposite directions.

The hybrid DNA pMYC1 and pMYC2 obtained in this experiment are hybrid DNAs of dsDNA Tmm-1 and pBR322. They can also be vectors for plant gene recombination.

Ip. Hybrid DNA of dsDNA Tmm-1 and yeast vector YRp7

The double-stranded DNA of MYMV was prepared as in experiment Ic.

In the procedure of experiment Ie, the double-stranded DNA was digested similarly with 3 microliters of Bam HI, and 1 microliter of a solution of the Bam HI-digested/alkaline phosphatase-treated product of YRp7 (DNA 1 microgram/microliter) was used instead of 1 microliter of the solution of the Bam HI-digested-/alkaline phosphatase-treated product of pBR322 (DNA 1 microgram/microliter). Otherwise, a hybrid DNA was constructed and the competent cells of E. coli HB101 were transformed with it in the same way as in experiment Ie.

The solution of the Bam HI-digested/alkaline phosphatase-treated product of YRp7 was prepared as in experiment Ie by using YRp7 DNA instead of pBR322 DNA. Then, by the same operation as in experiment Ie, the Bam HI-digested product was treated with BAP.

The competent cells of E. coli HB101 were transformed by the same procedure as in experiment Ie using the hybrid DNA obtained. Thus, 12 transformants were obtained. A mini-preparation of a plasmid DNA was carried out on the 12 transformants by the same boiling lysis method, and the plasmid DNAs were digested with Bam HI. Four hybrid plasmids containing a fragment with a size of 2.67 Kbp were obtained. Two of them were designated as YMYBp1 and YMYBp2. When YMYBp1 was digested with Bgl II, fragments with a size of 5.1, 1.77 and 1.65 Kbp were formed. When YMYBp2 was digested with Bgl II, fragments with a size of 4.6, 2.25 and 1.65 KbP were obtained. Bam HI fragments having a size of 2.67 Kbp were taken out from YMYBp1 and YMYBp2. When these DNA fragments were digested with Cla I, fragments having a size of 1.43 and 1.24 Kbp were formed from each of the 2.67 Kbp fragments.

Figure 7A:
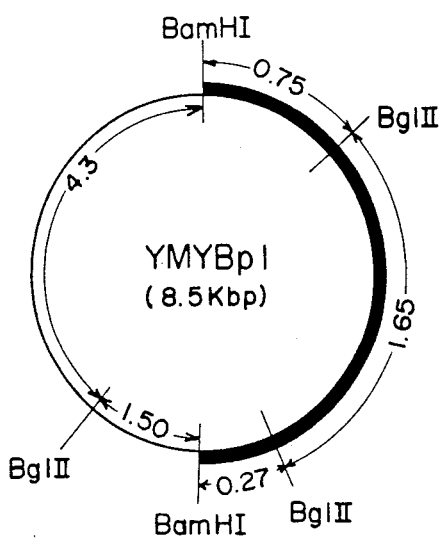
FIGS. 7(*a*) and 7(*b*), respectively, show hybrid DNAs YMBp1 and YMBp2 formed by the insertion of the Bam HI-cleaved DNA into the Bam HI site of YRp7 in opposite directions.
Figure 7B:
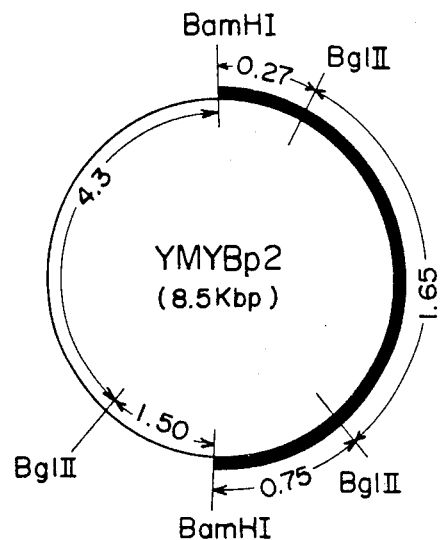

It is seen from the above results that as shown in FIGS. 7-(a) and -(b), YMYBp1 and YMYBp2 are hybrid DNAs formed by the insertion of the Bam HI-cleaved DNA into the Bam HI site of YRp7 in opposite directions.

Iq. Hybrid DNA of dsDNA Tmm-2 and yeast vector YIp32

In the same way as in experiment Ie, the double-stranded DNA of MYMV was digested with 3 microliters of Hind III, and 1 microliter (DNA 1 microgram/microliter) of a solution of the Hind III-digested/alkaline phosphatase-treated product of YIp32 (to be described below) was used instead of 1 microliter of the solution of the bam HI digested/alkaline phosphatase-treated product of pBR322 (DNA 1 microgram/microliter). Otherwise, by the same operation as in experiment Ie, a hybrid DNA ws constructed and the competent cells of E. coli HB101 were transformed.

The solution of the Hind III-digested/alkaline phosphatase-treated product of YIp32 was prepared in the same way as in experiment if except that YIp32 was used insteaed of pBR322. The YIp32 DNA was digested with Hind III and then treated with BAP.

By the same procedure as in experiment, Ie, the competent cells of E. coli HB101 were transformed with the hybrid DNA obtained. From 16 transformants, a plasmid DNA was separated by the boiling lysis method as in experiment Ie, and the resulting plamid DNA was digested with Hind III. Consequently, 4 hybrid plasmids containing a fragment with a size of 2.7 Kbp were obtained. Two of them were designated as YMYHp2 and YMYHp2. When YMYHp1 was digested with Pst I, fragments having a size of 6.2 and 3.2 Kbp were formed. When YMYHp2 was digested with Pat. I, fragments having a size of 8.3 and 1.12 Kbp were formed.

Hind III fragments having a size of 2.7 Kbp were taken out from YMYHp1 and YMYHp2, and digested wtih Pst I, fragments having a size of 2.4 and 0.34 Kbp were formed from each of the 2.7 Kpb fragments.

Figure 8A:
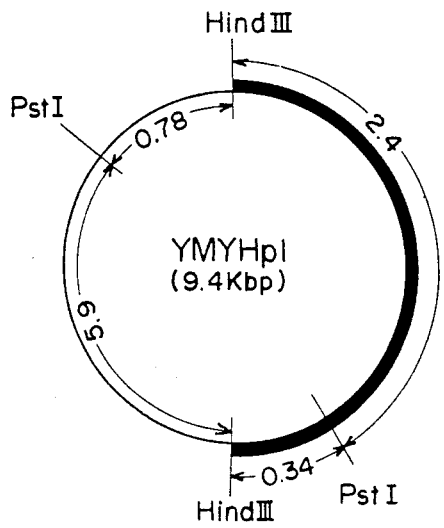
FIGS. 8(*A*) and 8(*b*), respectively, show hybrid DNAs formed by the insertion of the Hind III-digested DNA of dsDNA TMM-2 into the Hind III site of YIp32 in opposite directions.
Figure 8B:
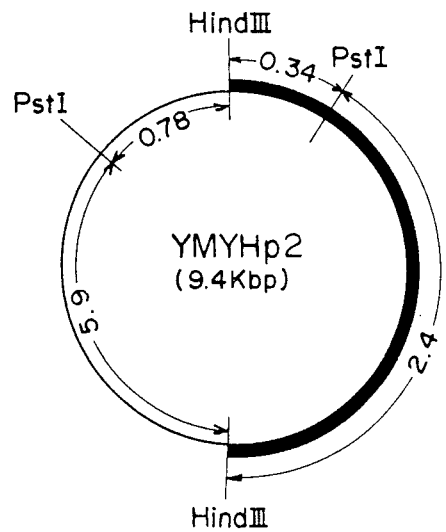

It is seen from the foregoing results that YMYHp1 and YMYHp2 are hybrid DNAs formed by the insertion of the Hind III-digested DNA of dsDNA TMM-2 into the Hind III site of YIp32 in opposite directions, as shown in FIGS. 8-(a) and -(b). TMM-1 and TMM-2 have been deposited and are available from the Fermentation Research Institute, Ibaraki, Japan.

What we claim is:

1. An isolated, substantially pure double-stranded DNA which is not digestible with restriction endonuclease Dpn I, having sequences complementary to a single-stranded DNA which has a molecular size of about 2.67 Kb and is derived from mungbean yellow mosaic virus, and giving the restriction endonuclease cleavage map shown in FIG. 1 of the accompanying drawings.

2. An isolated, substantially pure double-stranded DNA, which is not digestible with restriction endonuclease Mbo I, having sequences complementary to a single-stranded DNA which has a molecular size of about 2.67 Kb and is derived from mungbean yellow mosaic virus, and giving the restriction endonuclease cleavage map shown in FIG. 1 of the accompanying drawings.

3. The double-stranded DNA of claim 1 or 2 which is not digestible with restriction endonucleases Kpn I, Mlu I, Pvu I, Pvu II, Sal I, Xho I, Hind III, Pst I, Sac I, Sph I, Eco RV, Stu I, Nru I, Bcl I, Ban II, Apa I and Hpa I.

4. An isolated, substantially pure double-stranded DNA, which is not digestible with restriction endonuclease DPNI, having sequences complementary to a single-stranded DNA which has a molecular size of about 2.70 Kb and is derived from mungbean yellow mosaic virus, and giving the restriction endonuclease cleavage map shown in FIG. 2 of the accompanying drawings.

5. An isolated, substantially pure double-stranded DNA, which is not digestible with restriction endonuclease Mbo I, having sequences complementary to a single-stranded DNA which has a molecular size of about 2.70 Kb and is derived from mungbean yellow mosaic virus, and giving the restriction endonuclease cleavae map shown in FIG. 2 of the accompanying drawings.

6. The double-stranded DNA of claims 4 or 5 which is not digestible with restriction endonucleases Kpn I, Mlu I, Pvu II, Sal I, Xho I, Cla I, Xba I, Sac I, Bgl I, Sph I, Eco RV, Stu I, Nru I, Bcl I, Bst EII, AVa I, Apa I and Sma I.

7. A hybrid DNA consisting essentially of a host vector, and inserted into said host vector DNA, an isolated substantially pure double-stranded DNA which is digestible with the restriction endonuclease Mbo I, but is not digestible with restriction endonuclease Dpn I, having sequences complementary to a single-stranded DNA which has a molecular size of about 2.67 Kb and is derived form mungbean yellow mosaic virus, and giving the restriction endonuclease cleavage map shown in FIG. 1 of the accompanying drawings.

8. A hybrid DNA consisting essentially of a host vector DNA, and inserted into said vector DNA, an isolated substantially pure double-stranded DNA, which is digestible with the restriction endonuclease Dpn I, but is not digestible with restriction endonuclease Mbo I, having sequences complementary to a single-stranded DNA which has a molecular size of about 2.67 Kb and is derived from mungbean yellow mosaic virus, and giving the restriction endonuclease cleavage map shown in FIG. 1 of the accompanying drawings.

9. The hybrid DNA of claim 7 or 8 wherein the host vector DNA is selected from the group consisting of PBR322, PBR325 and pBR328 of *Eschericia coli* and YRp7 of *Saccharomyces cerevisiae*.

10. The hybrid DNA of claims 7 or 8 which has the ability of self-propagate in a member selected from the group consisting of *Eschericia coli*, *Saccharomyces cerevisiae* and *Bacillus subtilis*.

11. A hybrid DNA consisting essentially of a host vector DNA, and inserted into said host vector DNA, an isolated, substantially pure double-stranded DNA, which is digestible with the restriction endonuclease Mbo I, but is not digestible with restriction endonuclease Dpn I, having sequences complementary to a single-stranded DNA which has a molecular size of about 2.70 Kb and is derived from mungbean yellow mosaic virus, and giving the restriction endonuclease cleavage map shown in FIG. 2 of the accompanying drawings.

12. A hybrid DNA consisting essentially of a host vector DNA, and inserted into said host vector DNA, an isolated, substantially pure double-stranded DNA, which is digestible with the restriction endonuclease Dpn I, but is not digestible with restriction endonuclease Mbo I, having sequences complementary to a single-stranded DNA which has a molecular size of about 270 Kb and is derived from mungbean yellow mosaic virus, and giving the restriction endonuclease cleavage map shown in FIG. 2 or the accompanying drawings.

13. The hybrid DNA of claim 11 or claim 12 wherein the host vector DNA is selected from the group consisting of pBR322, pBR325 and pBR328 of *Escherichia coli* and YIp 32 of *Saccharomyces cerevisiae*.

14. The hybrid DNA of claims 11 or 12 which has the ability to self-propagate in a member selected from the group consisting of *Eschericia coli*, *Saccharomyces cerevisiae* and *Bacillus subtilis*.

* * * * *